(12) United States Patent
Lazar et al.

(10) Patent No.: US 9,102,739 B2
(45) Date of Patent: Aug. 11, 2015

(54) ANTI-GLYPICAN-3 ANTIBODY

(75) Inventors: Gregory Alan Lazar, Los Angeles, CA (US); Bassil I. Dahiyat, Altadena, CA (US); Hisafumi Okabe, Kanagawa (JP); Masamichi Sugimoto, Kanagawa (JP); Shigeyuki Iijima, Shizuoka (JP); Izumi Sugo, Shizuoka (JP)

(73) Assignees: Chugai Seiyaku Kabushiki Kaisha, Tokyo (JP); Xencor, Inc., Monrovia, CA (US)

( * ) Notice: Subject to any disclaimer, the term of this patent is extended or adjusted under 35 U.S.C. 154(b) by 355 days.

(21) Appl. No.: 12/089,957

(22) PCT Filed: Oct. 11, 2006

(86) PCT No.: PCT/US2006/039682
§ 371 (c)(1),
(2), (4) Date: Jul. 2, 2008

(87) PCT Pub. No.: WO2007/047291
PCT Pub. Date: Apr. 26, 2007

(65) Prior Publication Data
US 2008/0267979 A1 Oct. 30, 2008

Related U.S. Application Data

(63) Continuation of application No. 11/251,561, filed on Oct. 14, 2005, now abandoned.

(51) Int. Cl.
| | |
|---|---|
| *C07K 16/00* | (2006.01) |
| *C12P 21/08* | (2006.01) |
| *C12P 21/06* | (2006.01) |
| *A61K 39/395* | (2006.01) |
| *A61K 39/40* | (2006.01) |
| *C07K 16/30* | (2006.01) |
| *C07K 1/00* | (2006.01) |
| *A61K 39/00* | (2006.01) |

(52) U.S. Cl.
CPC ......... *C07K 16/303* (2013.01); *A61K 2039/505* (2013.01); *C07K 2317/24* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 6,165,745 | A | 12/2000 | Ward et al. |
| 6,210,670 | B1 | 4/2001 | Berg |
| 6,737,056 | B1 | 5/2004 | Presta |
| 7,297,775 | B2 | 11/2007 | Idusogie et al. |
| 7,317,091 | B2 * | 1/2008 | Lazar et al. ............... 530/387.1 |
| 7,361,336 | B1 | 4/2008 | Bergstein |
| 7,427,400 | B2 | 9/2008 | Bergstein |
| 7,662,925 | B2 * | 2/2010 | Lazar et al. ............... 530/387.1 |
| 7,867,734 | B2 | 1/2011 | Nakano et al. |
| 7,871,613 | B2 | 1/2011 | Kinoshita et al. |
| 7,919,086 | B2 | 4/2011 | Nakano et al. |
| 8,039,592 | B2 | 10/2011 | Lazar et al. |
| 2003/0103970 | A1 | 6/2003 | Tsuchiya et al. |
| 2003/0175884 | A1 | 9/2003 | Umana et al. |
| 2004/0024320 | A1 | 2/2004 | Karasawa et al. |
| 2004/0132101 | A1 | 7/2004 | Lazar et al. |
| 2004/0236080 | A1 | 11/2004 | Aburatani et al. |
| 2005/0171339 | A1 | 8/2005 | Sugo et al. |
| 2005/0233392 | A1 | 10/2005 | Filmus et al. |
| 2006/0024298 | A1 | 2/2006 | Lazar et al. |
| 2006/0040325 | A1 | 2/2006 | Wu et al. |
| 2006/0167232 | A1 | 7/2006 | Aburatani et al. |
| 2006/0188510 | A1 | 8/2006 | Aburatani et al. |
| 2006/0287508 | A1 | 12/2006 | Sugo et al. |
| 2007/0087005 | A1 | 4/2007 | Lazar et al. |
| 2007/0172488 | A1 | 7/2007 | Aburatani et al. |
| 2007/0190599 | A1 | 8/2007 | Nakano et al. |
| 2007/0269444 | A1 | 11/2007 | Kinoshita et al. |
| 2008/0008710 | A1 | 1/2008 | Aburatani et al. |
| 2008/0051563 | A1 | 2/2008 | Lazar et al. |
| 2008/0124330 | A1 | 5/2008 | Nakano et al. |
| 2008/0154025 | A1 | 6/2008 | Lazar et al. |
| 2008/0161541 | A1 | 7/2008 | Lazar et al. |
| 2008/0166756 | A1 | 7/2008 | Tsuchiya et al. |
| 2008/0181890 | A1 | 7/2008 | Lazar et al. |

(Continued)

FOREIGN PATENT DOCUMENTS

| | | |
|---|---|---|
| CA | 2481658 | 10/2003 |
| CA | 2497744 | 3/2004 |

(Continued)

OTHER PUBLICATIONS

Ho et al. European Journal of Cancer. 2011; 47:333-338.*
Lund et al., "Multiple interactions of IgG with its core oligosaccharide can modulate recognition by complement and human Fc$\gamma$receptor I and influence the synthesis of its oligosaccharide chains," Journal Immunol., 157:4963-69 (1996).
Ohno et al., "Antigen-binding specificities of antibodies are primarily determined by seven residues of VH," Proc. Natl. Acad. Sci. U.S.A., 82:2945-49 (1985).

(Continued)

*Primary Examiner* — Chun Dahle
(74) *Attorney, Agent, or Firm* — Fish & Richardson P.C.

(57) ABSTRACT

An anti-glypican-3 antibody comprising one or more amino acid substitutions introduced in the Fc region is disclosed. Preferably, in the anti-glypican-3 antibody, one or more of the amino acid residues at the positions 239, 298, 326, 330 and 332 in the Fc region are substituted with other amino acid residues. Since the Fc-modified anti-glypican-3 antibody of the invention exhibit enhanced ADCC activity, it is useful in treating cancers, such as hepatic cancer. Also disclosed are an anticancer agent comprising the anti-glypican-3 antibody of the invention and a pharmaceutically acceptable carrier, as well as a method of treating a patient with cancer comprising administering to the patient the anticancer agent of the invention.

24 Claims, 5 Drawing Sheets

(56) References Cited

U.S. PATENT DOCUMENTS

| | | | |
|---|---|---|---|
| 2009/0060907 | A1 | 3/2009 | Aburatani et al. |
| 2010/0183595 | A1 | 7/2010 | Aburatani et al. |
| 2010/0248359 | A1 | 9/2010 | Nakano et al. |
| 2011/0033452 | A1 | 2/2011 | Nakano et al. |
| 2011/0091907 | A1 | 4/2011 | Kataoka et al. |
| 2011/0104157 | A1 | 5/2011 | Kinoshita et al. |

FOREIGN PATENT DOCUMENTS

| | | |
|---|---|---|
| CN | 1277632 | 12/2000 |
| EP | 1 176 195 | 1/2002 |
| EP | 1 331 266 | 7/2003 |
| EP | 1 411 118 | 4/2004 |
| EP | 1 462 799 | 9/2004 |
| EP | 1 464 702 | 10/2004 |
| EP | 1 498 491 | 1/2005 |
| EP | 1 541 680 | 6/2005 |
| EP | 1 548 442 | 6/2005 |
| EP | 1 561 686 | 6/2005 |
| EP | 1 671 645 | 6/2006 |
| EP | 1 674 111 | 6/2006 |
| EP | 1 800 693 | 6/2007 |
| EP | 1 816 140 | 8/2007 |
| JP | 2-42355 | 2/1990 |
| JP | 4-336051 | 11/1992 |
| JP | 11-118775 | 4/1999 |
| JP | 2001-108661 | 4/2001 |
| JP | 2002-48867 | 2/2002 |
| JP | 2003-149213 | 5/2003 |
| JP | 2004-053360 | 2/2004 |
| WO | WO9322332 | 11/1993 |
| WO | WO9823289 | 6/1998 |
| WO | WO 99/54342 | 10/1999 |
| WO | WO 00/61739 | 10/2000 |
| WO | WO 02/22739 | 3/2002 |
| WO | WO 02/31140 | 4/2002 |
| WO | WO 02/079255 | 10/2002 |
| WO | WO 03/000883 | 1/2003 |
| WO | WO 03/042686 | 5/2003 |
| WO | WO 03/057881 | 7/2003 |
| WO | WO 03/074679 | 9/2003 |
| WO | WO 03/085119 | 10/2003 |
| WO | WO 03/100429 | 12/2003 |
| WO | WO 2004/018667 | 3/2004 |
| WO | WO 2004/022597 | 3/2004 |
| WO | WO 2004/022739 | 3/2004 |
| WO | WO 2004/022754 | 3/2004 |
| WO | WO 2004/023145 | 3/2004 |
| WO | WO 2004/038420 | 5/2004 |
| WO | WO 2004/099249 | 11/2004 |
| WO | WO 2005/023301 | 3/2005 |
| WO | WO 2006/006693 | 1/2006 |
| WO | WO 2006/022407 | 3/2006 |
| WO | WO 2006/046751 | 5/2006 |
| WO | WO 2009/041643 | 4/2009 |
| WO | WO 2009/122667 | 10/2009 |

OTHER PUBLICATIONS

Roitt et al., "Immunology," Moscow, 102, 106-107 (2000).
Fish & Richardson P.C., Amendment in Reply to Action dated May 11, 2010 in U.S. Appl. No. 11/574,091, filed Aug. 11, 2010, 6 pages.
USPTO Notice of Allowance in U.S. Appl. No. 11/574,091, dated Aug. 31, 2010, 6 pages.
Fish & Richardson P.C., Amendment in Reply to Office Action dated May 21, 2010 in U.S. Appl. No. 11/577,944, filed Jun. 9, 2010, 5 pages.
USPTO Notice of Allowance in U.S. Appl. No. 11/577,944, dated Aug. 26, 2010, 6 pages.
Winter et al., "Humanized antibodies," Immunol. Today, 14:243-246 (1993).
Arii et al., "Characteristics of recurrent hepatocellular carcinoma in Japan and our surgical experience," J. Hepatobiliary Pancreat. Surg. 8:397-403 (2001).
Budhu et al., "The Molecular Signature of Metastases of Human Hepatocellular Carcinoma," Oncology, 69(suppl 1):23-27 (2005).
Rudikoff et al., "Single amino acid substitution altering antigen-binding specificity," Proc. Natl. Acad. Sci. USA, 79:1979-83 (1982).
Tang et al., "Metastatic human hepatocellular carcinoma models in nude mice and cell line with metastatic potential," World J. Gastroenterol., 7:597-601 (2001).
Fish & Richardson P.C., Amendment in Reply to Action dated Jun. 26, 2009 in U.S. Appl. No. 10/583,795, filed Dec. 24, 2009, 17 pages.
Fish & Richardson P.C., Amendment in Reply to Office Action dated Apr. 28, 2009 in U.S. Appl. No. 11/577,944, filed Oct. 27, 2009, 15 pages.
USPTO Final Office Action in U.S. Appl. No. 11/577,944, dated Jan. 20, 2010, 47 pages.
USPTO Restriction Requirement in U.S. Appl. No. 10/526,741, dated Mar. 27, 2006, 5 pages.
Davidson, Davidson & Kappel, LLC, Response to Restriction Requirement dated Mar. 27, 2006 in U.S. Appl. No. 10/526,741, filed Apr. 25, 2006, 6 pages.
USPTO Office Action in U.S. Appl. No. 10/526,741, dated Jun. 14, 2006, 40 pages.
Davidson, Davidson & Kappel, LLC, Amendment in Reply to Office Action dated Jun. 14, 2006 in U.S. Appl. No. 10/526,741, filed Dec. 12, 2006, 18 pages.
USPTO Final Office Action in U.S. Appl. No. 10/526,741, dated Mar. 9, 2007, 17 pages.
Davidson, Davidson & Kappel, LLC, Amendment in Reply to Office Action dated Mar. 9, 2007 in U.S. Appl. No. 10/526,741, filed Jul. 9, 2007, 9 pages.
USPTO Advisory Action in U.S. Appl. No. 10/526,741, dated Aug. 14, 2007, 3 pages.
USPTO Office Action in U.S. Appl. No. 10/526,741, dated Nov. 21, 2007, 17 pages.
Davidson, Davidson & Kappel, LLC, Amendment in Reply to Action dated Nov. 21, 2007 in U.S. Appl. No. 10/526,741, filed Mar. 20, 2008, 10 pages.
USPTO Final Office Action in U.S. Appl. No. 10/526,741, dated Jul. 9, 2008, 11 pages.
Davidson, Davidson & Kappel, LLC, Amendment in Reply to Office Action dated Jul. 9, 2008 in U.S. Appl. No. 10/526,741, filed Jan. 5, 2009, 113 pages.
USPTO Advisory Action in U.S. Appl. No. 10/526,741, dated Jan. 21, 2009, 4 pages.
USPTO Office Action in U.S. Appl. No. 10/526,741, dated Sep. 1, 2009, 15 pages.
Davidson, Davidson & Kappel, LLC, Amendment in Reply to Office Action dated Sep. 1, 2009 in U.S. Appl. No. 10/526,741, filed Feb. 24, 2010, 10 pages.
Fish & Richardson P.C., Amendment in Reply to Action dated Sep. 2, 2009 in U.S. Appl. No. 11/574,091, filed Mar. 2, 2010, 7 pages.
Ghetie et al., "Multiple Roles for the Major Histocompatibility Complex Class I-Related Receptor FcRn," Annu. Rev. Immunol., 18:739-766 (2000).
Hinton et al,. "Engineered Human IgG Antibodies with Longer Serum Half-lives in Primates," J. Biol. Chem., 279:6213-16 (2004).
Kim et al., "Mapping the site on human IgG for binding of the MHC class I-related receptor, FcRn," Eur. J. Immunol., 29:2819-25 (1999).
Martin et al., "Crystal Structure at 2.8 A of an FcRn/Heterodimeric Fc Complex: Mechanism of pH-Dependent Binding," Mol. Cell, 7:867-877 (2001).
Medesan et al., "Delineation of the Amino Acid Residues Involved in Transcytosis and Catabolism of Mouse IgG1," J. Immunol., 158:2211-17 (1997).
Raghavan et al., "Fc Receptors and their Interactions with Immunoglobulins," Annu. Rev. Cell Dev. Biol., 12:181-220 (1996).
USPTO Notice of Allowance in U.S. Appl. No. 10/583,795, dated Mar. 10, 2010, 16 pages.
Davidson, Davidson & Kappel, LLC, Amendment in Reply to Action dated Aug. 14, 2007 in U.S. Appl. No. 10/526,741, filed Sep. 6, 2007, 9 pages.
Fish & Richardson P.C., Reply to Action dated Feb. 25, 2009 in U.S. Appl. No. 11/251,561, filed Mar. 24, 2010, 4 pages.

(56) References Cited

OTHER PUBLICATIONS

Fish & Richardson P.C., Supplemental Amendment in Reply to Action dated Feb. 25, 2009 in U.S. Appl. No. 11/251,561, filed Mar. 26, 2010, 16 pages.
USPTO Final Office Action in U.S. Appl. No. 11/574,091, dated May 11, 2010, 16 pages.
Fish & Richardson P.C., Amendment in Reply to Office Action dated Jan. 20, 2010 in U.S. Appl. No. 11/577,944, filed Apr. 29, 2010, 6 pages.
USPTO Interview Summary in U.S. Appl. No. 11/577,944, dated May 3, 2010, 3 pages.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-38 (1990).
Lazar et al., "Transforming Growth Factor alpha: Mutation of Aspartic Acid 47 and Leucine 48 Results in Different Biological Activities," Mol. Cell. Biol., 8:1247-52 (1988).
USPTO Non-Final Office Action in U.S. Appl. No. 11/577,944, dated May 21, 2010, 16 pages.
USPTO Office Action in U.S. Appl. No. 10/481,524, dated Apr. 3, 2006, 23 pages.
Davidson, Davidson & Kappel, LLC, Amendment in Reply to Office Action dated Apr. 3, 2006 in U.S. Appl. No. 10/481,524, filed Aug. 31, 2006, 9 pages.
USPTO Interview Summary in U.S. Appl. No. 10/481,524, dated Sep. 6, 2006, 3 pages.
USPTO Restriction Requirement in U.S. Appl. No. 10/481,524, dated Jan. 5, 2007, 4 pages.
USPTO Office Communication in U.S. Appl. No. 10/481,524, dated Jan. 23, 2007, 2 pages.
USPTO Restriction Requirement in U.S. Appl. No. 11/702,780, dated Jul. 24, 2007, 5 pages.
Davidson, Davidson & Kappel, LLC, Response to Restriction Requirement dated Jul. 24, 2007 in U.S. Appl. No. 11/702,780, filed Aug. 22, 2007, 4 pages.
USPTO Office Action in U.S. Appl. No. 11/702,780, dated Nov. 16, 2007, 9 pages.
USPTO Interview Summary in U.S. Appl. No. 11/702,780, dated Dec. 14, 2007, 4 pages.
Davidson, Davidson & Kappel, LLC, Amendment in Reply to Office Action dated Nov. 16, 2007 in U.S. Appl. No. 11/702,780, filed May 16, 2008, 11 pages.
USPTO Office Action in U.S. Appl. No. 11/702,780, dated Sep. 3, 2008, 9 pages.
Davidson, Davidson & Kappel, LLC, Amendment in Reply to Office Action dated Sep. 3, 2008 in U.S. Appl. No. 11/702,780, filed Dec. 29, 2008, 6 pages.
USPTO Advisory Action in U.S. Appl. No. 11/702,780, dated Jan. 13, 2009, 4 pages.
USPTO Office Action in U.S. Appl. No. 11/702,780, dated Apr. 2, 2009, 7 pages.
Davidson, Davidson & Kappel, LLC, Amendment in Reply to Office Action dated Apr. 2, 2009 in U.S. Appl. No. 11/702,780, filed Sep. 30, 2009, 215 pages.
USPTO Notice of Allowance in U.S. Appl. No. 11/702,780, dated Jan. 26, 2010, 5 pages.
Nakano et al., "Anti-glypican 3 antibodies cause ADCC against human hepatocellular carcinoma cells," Biochem. Biophys. Res. Comm., 378:279-284 (2009).
Partial European Search Report for App. Ser. No. 10 00 3424 dated Jun. 7, 2010, 11 pages.
Abe et al., "Matrixeye™ Portable 3D Ultrasonic Inspection System," Toshiba Review, 60:48-51 (2005).
Bendayan, "Possibilities of False Immunocytochemical Results Generated by the Use of Monoclonal Antibodies: The Example of the Anti-Proinsulin Antibody," J. Histochem. Cytochem., 43:881-886 (1995).
Bost et al., "Antibodies Against a Peptide Sequence within the HIV Envelope Protein Crossreacts with Human Interleukin-2," Immunol. Invest., 17:577-586 (1988).
Brorson et al., "Mutational Analysis of Avidity and Fine Specificity of Anti-Levan Antibodies," J. Immunol., 163:6694-6701 (1999).
Brummell et al., "Probing the combining site of an anti-carbohydrate antibody by saturation-mutagenesis: role of the heavy-chain CDR3 residues," Biochemistry, 32:1180-87 (1993).
Burks et al., "In vitro scanning saturation mutagenesis of an antibody binding pocket," Proc. Natl. Acad. Sci. USA, 94:412-417 (1997).
Capurro et al., "Glypican-3: A novel serum and histochemical marker for hepatocellular carcinoma," Gastroenterology, 125:89-97 (2003).
Cappuro et al., "Overexpression of Glypican-3 in Human Hepatocellular Carcinomas Determined by Immunohistochemistry Using a Monocolonal Antibody," Proceedings of the Annual Meeting of the American Association for Cancer Research, 93rd Annual Meeting, Apr. 6-10, 2002, 43:219 Abstract #1097 (2002).
Carter, "Improving the efficacy of antibody-based cancer therapies," Nat. Rev. Cancer, 1:118-129 (2001).
Casset et al., "A peptide mimetic of an anti-CD4 monoclonal antibody by rational design," Biochem. Biophys. Res. Commun., 307:198-205 (2003).
Chen et al., "Selection and Analysis of an Optimized Anti-VEGF Antibody: Crystal Structure of an Affinity-Matured Fab in Complex with Antigen," J. Mol. Biol., 293:865-881 (1999).
Colman, "Effects of amino acid sequence changes on antibody-antigen interactions," Res. Immunol., 145:33-36 (1994).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 169:3076-84 (2002).
Dennis, "Cancer: Off by a whisker," Nature, 442:739-741 (2006).
Dufner et al., "Harnessing phage and ribosome display for antibody optimization," Trends Biotechnol., 24:523-529 (2006).
Filmus, "Glypicans in Growth Control and Cancer," Glycobiology, 11:19R-23R (2001).
Gonzalez et al., "OCI-5/GPC3, A Glypican Encoded by a Gene That is Mutated in the Simpson-Golabi-Behmel Overgrowth Syndrome, Induces Apoptosis in a Cell Line-Specific Manner,"J. Cell Biol., 141:1407-14 (1998).
Gura, "Systems for Identifying New Drugs Are Often Faulty," Science, 278:1041-42 (1997).
Hippo et al., "Identification of Soluble $NH_2$-Terminal Fragment of Glypican-3 as a Serological Marker for Early-Stage Hepatocellular Carcinoma," Cancer Res., 64:2418-23 (2004).
Holm et al., "Functional mapping and single chain construction of the anti-cytokeratin 8 monoclonal antibody TS1," Mol. Immunol., 44:1075-84 (2007).
Huber, "Structure and Function of the Human Glypican 3 Gene," Washington University, Division of Biology and Biomedical Sciences Program in Molecular Genetics, St. Louis, Missouri (1998).
Jiang et al., "Recurrence or metastasis of HCC: predictors, early detection and experimental antiangiogenic therapy," World J. Gastroenterol., 6:61-65 (2000).
Jang et al., "The structural basis for DNA binding by an anti-DNA autoantibody," Mol. Immunol., 35:1207-17 (1998).
Kobayashi et al., "Tryptophan H33 plays an important role in pyrimidine (6-4) pyrimidone photoproduct binding by a high-affinity antibody," Protein Eng., 12:879-884 (1999).
Kumar et al., "Molecular Cloning and Expression of the Fabs of Human Autoantibodies in Escherichia coli," J. Biol. Chem., 275:35129-36 (2000).
Lage et al., "Cloning and Characterization of Human cDNAs Encoding a Protein with High Homology to Rat Intestinal Development Protein OCI-5," Gene, 188:151-156 (1997).
Lage et al., "Expression of a glypican-related 62-kDa antigen is decreased in hepatocellular carcinoma in correspondence to the grade of tumor differentiation," Virchows Arch., 438:567-573 (2001).
MacCallum et al., "Antibody-antigen Interactions: Contact Analysis and Binding Site Topography," J. Mol. Biol., 262:732-745 (1996).

(56) References Cited

OTHER PUBLICATIONS

Man et al., "Upregulation of Glypican-3 Expression in Hepatocellular Carcinoma but Downregulation in Cholangiocarcinoma Indicates its Differential Diagnosis Value in Primary Liver Cancers," *Liver Int.*, 25:962-966 (2005).
Midorikawa et al., "Glypican-3, Overexpressed in Hepatocellular Carcinoma, Modulates FGF2 and BMP-7 Signaling," *Int. J Cancer*, 103:445-465 (2003).
MSNBC News Service, "Mixed results on new cancer drug," 4 pages (2000).
Nakatsura et al., "Glypican-3, overexpressed specifically in human hepatocellular carcinoma, is a novel tumor marker," *Biochem. Biophys. Res. Commun.*, 306:16-25 (2003).
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," *Cancer Res.*, 64:2127-33 (2004).
Pilia et al., "Mutations in GPC3, A Glypican Gene, Cause the Simpson-Golabi-Behmel Overgrowth Syndrome," *Nature Genet.*, 12:241-247 (1996).
Presta, "Engineering Antibodies for Therapy," *Curr. Pharm. Biotechnol.*, 3:237-356 (2002).
Roskams et al., "Heparan sulphate proteoglycan expression in human primary liver tumours," *J. Pathol.*, 185:290-297 (1998).
Sabit et al., "Enhanced expression of basement-membrane-type heparan sulfate proteoglycan in tumor fibro-myxoid stroma of intrahepatic cholangiocarcinoma," *Pathol. Int*, 51:248-256 (2001).
Seaver, "Monoclonal Antibodies in Industry: More Difficult Than Originally Thought," *Genetic Engineering*, 14:10, 21 (1994).
Shields et al., "Lack of fucose on human IgG1 N-linked oligosaccharide improves binding to human Fcgamma RIII and antibody-dependent cellular toxicity," *J Biol. Chem.*, 277:26733-40 (2002).
Shinkawa et al., "The absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-73 (2003).
Smith-Gill et al., "Contributions of immunoglobulin heavy and light chains to antibody specificity for lysozyme and two haptens," *J Immunol.*, 139:4135-44 (1987).
Song et al., "Light Chain of Natural Antibody Plays a Dominant Role in Protein Antigen Binding," *Biochem. Biophys. Res. Commun.*, 268:390-394 (2000).
Steplewski et al., Biological activity of human-mouse IgG1, IgG2, IgG3, and IgG4 chimeric monoclonal antibodies with antitumor specificity, *Proc. Natl. Acad. Sci. USA*, 85:4852-4856 (1988).
Sung et al., "Glypican-3 is overexpressed in human hepatocellular carcinoma," *Cancer Sci.*, 94:259-262 (2003).
Vajdos et al., "Comprehensive Functional Maps of the Antigen-binding Site of an Anti-ErbB2 Antibody Obtained with Shotgun Scanning Mutagenesis," *J. Mol. Biol.*, 320:415-428 (2002).
Voskoglou-Nomikos et al., "Clinical Predictive Value of the in Vitro Cell Line, Human Xenograft, and Mouse Allograft Preclinical Cancer Models," *Clin. Cancer Res.*, 9:4227-39 (2003).
Yamaguchi et al., "Current Status and Future Perspective of Biotherapy for Cancer," *Biotherapy*, 13:747-753 (1999) (English summary included).
Yamane-Ohnuki et al., "Establishment of *FUT8* Knockout Chinese Hamster Ovary Cells: An Ideal Host Cell Line for Producing Completely Defucosylated Antibodies With Enhanced Antibody-Dependent Cellular Cytotoxicity," *Biotechnol. Bioeng.*, 87:614-622 (2004).
Wichert et al., "Glypican-3 is involved in cellular protection against mitoxantrone in gastric carcinoma cells," *Oncogene*, 23:945-955 (2004).
Wu et al., "Humanization of a Murine Monoclonal Antibody by Simultaneous Optimization of Framework and CDR Residues," *J. Mol. Biol.*, 294:151-162 (1999).
USPTO Restriction Requirement in U.S. Appl. No. 11/251,561, dated Dec. 13, 2007, 9 pages.
Fish & Richardson P.C., Response to Restriction Requirement dated Dec. 13, 2007 in U.S. Appl. No. 11/251,561, filed Feb. 12, 2008, 1 page.
USPTO Office Action in U.S. Appl. No. 11/251,561, dated May 14, 2008, 12 pages.
Fish & Richardson P.C., Amendment in Reply to Action dated May 14, 2008 in U.S. Appl. No. 11/251,561, filed Nov. 13, 2008, 8 pages.
USPTO Final Office Action in U.S. Appl. No. 11/251,561, dated Feb. 25, 2009, 13 pages.
International Search Report and Written Opinion for App. Ser. No. PCT/US2006/039682 dated Apr. 13, 2007, 13 pages.
USPTO Restriction Requirement in U.S. Appl. No. 10/583,795, dated Dec. 18, 2007, 5 pages.
Fish & Richardson P.C., Response to Restriction Requirement dated Dec. 18, 2007 in U.S. Appl. No. 10/583,795, filed Jan. 18, 2008, 19 pages.
USPTO Office Action in U.S. Appl. No. 10/583,795, dated Mar. 27, 2008, 42 pages.
Fish & Richardson P.C., Amendment in Reply to Action dated Mar. 27, 2008 in U.S. Appl. No. 10/583,795, filed Sep. 29, 2008, 46 pages.
USPTO Office Action in U.S. Appl. No. 10/583,795, dated Jan. 7, 2009, 25 pages.
Interview Summary in U.S. Appl. No. 10/583,795, dated Apr. 8, 2009, 2 pages.
Fish & Richardson P.C., Amendment in Reply to Action dated Jan. 7, 2009 in U.S. Appl. No. 10/583,795, filed Apr. 7, 2009, 13 pages.
Interview Summary in U.S. Appl. No. 10/583,795, dated Apr. 20, 2009, 2 pages.
USPTO Office Action in U.S. Appl. No. 10/583,795, dated Jun. 26, 2009, 19 pages.
Japanese Patent Office, International Search Report for App. Ser. No. PCT/JP2005/013103, mailed Oct. 25, 2005, 1 page.
International Preliminary Report on Patentability for App. Ser. No. PCT/JP2005/013103, dated Jan. 7, 2009, 4 pages.
European Search Report for App. Ser. No. EP 05 76 0156, dated Oct. 1, 2007, 15 pages.
USPTO Restriction Requirement in U.S. Appl. No. 10/570,647, dated Apr. 4, 2008, 6 pages.
Japanese Patent Office, International Search Report for App. Ser. No. PCT/JP2004/013183, mailed Nov. 30, 2004, 4 pages.
Japanese Patent Office, International Preliminary Report on Patentability for App. Ser. No. PCT/JP2004/013183, dated Sep. 1, 2005, 17 pages.
European Search Report for App. Ser. No. EP 04 77 2 922, dated Jun. 14, 2007, 2 pages.
USPTO Restriction Requirement in U.S. Appl. No. 11/574,091, dated Dec. 17, 2008, 8 pages.
Fish & Richardson P.C., Response to Restriction Requirement dated Dec. 17, 2008 in U.S. Appl. No. 11/574,091, filed Jun. 16, 2009, 1 page.
USPTO Office Action in U.S. Appl. No. 11/574,091, dated Sep. 2, 2009, 18 pages.
Japanese Patent Office, International Search Report for App. Ser. No. PCT/JP2005/015607, mailed Oct. 24, 2005, 3 pages.
European Search Report for App. Ser. No. EP 05 78 0979, dated Nov. 10, 2008, 5 pages.
USPTO Office Action in U.S. Appl. No. 11/577,944, dated Apr. 28, 2009, 14 pages.
Japanese Patent Office, International Search Report for App. Ser. No. PCT/JP2005/020057, mailed Jan. 24, 2006, 2 pages.
European Search Report for App. Ser. No. EP 05 80 0031, dated Jul. 31, 2009, 9 pages.
Search Report and Written Opinion for App. Ser. No. SG 200703074-5, mailed Jul. 21, 2008, 9 pages.
USPTO Non-Final Office Action in U.S. Appl. No. 11/251,561, dated Aug. 4, 2011, 15 pages.
Office Action for Canadian App. Ser. No. 2,544,692, dated Aug. 1, 2011, 6 pages.
Fish & Richardson P.C., Amendment in Reply to Action dated Jun. 27, 2012 in U.S. Appl. No. 12/797,349, filed Dec. 27, 2012, 14 pages.
USPTO Interview Summary in U.S. Appl. No. 11/251,561, dated Dec. 31, 2012, 3 pages.

(56) References Cited

OTHER PUBLICATIONS

Fish & Richardson P.C., Response to Restriction Requirement dated Aug. 21, 2012 in U.S. Appl. No. 12/852,950, filed Feb. 5, 2013, 1 page.
USPTO Restriction Requirement in U.S. Appl. No. 12/852,950, Feb. 25, 2013, 7 pages.
Fish & Richardson P.C., Amendment in Reply to Action dated Aug. 4, 2011 in U.S. Appl. No. 11/251,561, filed Feb. 6, 2012, 24 pages.
USPTO Final Office Action in U.S. Appl. No. 11/251,561, dated May 2, 2012, 21 pages.
Baneyx, "Recombinant protein expression in *Escherichia coli*," *Curr. Opin. Biotechnol.*, 10:411-421 (1999).
Carter et al., "Humanization of an anti-p185HER2 antibody for human cancer therapy," *Proc. Natl. Acad. Sci. U.S.A.*, 89:4285-4289 (1992).
Houdebine, "Production of pharmaceutical proteins from transgenic animals," *J. Biotechnol.*, 34:269-287 (1994).
Kappel et al., "Regulating gene expression in transgenic animals" *Curr. Opin. Biotechnol.*, 3:548-553 (1992).
Paul, "Structure and function of immunoglobulins," Fundamental Immunology, Third Edition, 292-295 (1993).
Portolano et al., "Lack of promiscuity in autoantigen-specific H and L chain combinations as revealed by human H and L chain 'roulette'," *J. Immunol.*, 150:880-887 (1993).
Soderlind et al., "The immune diversity in a test tube—non-immunised antibody libraries and functional variability in defined protein scaffolds," *Comb. Chem. High Throughput Screen.*, 4:409-416 (2001).
Wall, "Transgenic Livestock: Progress and Prospects for the Future," *Theriogenology*, 45:57-68 (1996).
Office Action for Canadian App. Ser. No. 2,585,196, dated May 29, 2012, 3 pages.
USPTO Non-Final Office Action in U.S. Appl. No. 12/797,349, dated Jun. 27, 2012, 27 pages.
Pannetier et al., "The sizes of the CDR3 hypervariable regions of the murine T-cell receptor beta chains vary as a function of the recombined germ-line segments," *Proc. Natl. Acad. Sci. U.S.A.*, 90: 4319-4323 (1993).
Wu et al., "Length distribution of CDRH3 in antibodies," *Proteins*, 16:1-7 (1993).
Fish & Richardson P.C., Amendment and Reply to Restriction Requirement dated Feb. 25, 2013 in U.S. Appl. No. 12/852,950, filed Jun. 25, 2013, 14 pages.
Fish & Richardson P.C., Amendment in Reply to Office Action dated May 2, 2012 in U.S. Appl. No. 11/251,561, filed May 22, 2013, 16 pages.
Fish & Richardson P.C., Amendment in Reply to Office Action dated Apr. 25, 2013 in U.S. Appl. No. 12/797,349, filed Aug. 23, 2013, 9 pages.
Tamura et al., "Structural correlates of an anticarcinoma antibody: identification of specificity-determining residues (SDRs) and development of a minimally immunogenic antibody variant by retention of SDRs only," *J. Immunol.*, 164(3):1432-1441 (2000).
USPTO Restriction Requirement in U.S. Appl. No. 12/852,950, dated Aug. 21, 2012, 7 pages.
Office Action for Canadian App. Ser. No. 2,544,692, dated Sep. 4, 2012, 3 pages.
Greenspan et al., "Defining epitopes: It's not as easy as it seems," *Nat. Biotechnol.*, 17:936-7 (1999).
Johnson et al., "The Kabat database and a bioinformatics example," *Methods Mol. Biol.*, 248:11-25 (2004).
Panka et al., Variable region framework differences result in decreased or increased affinity of variant anti-digoxin antibodies, *Proc. Natl. Acad. Sci. U.S.A.*, 85:3080-4 (1988).
USPTO Non-Final Office Action in U.S. Appl. No. 12/797,349, dated Apr. 25, 2013, 20 pages.
Caldas et al., "Humanization of the anti-CD18 antibody 6.7: an unexpected effect of a framework residue in binding to antigen," *Mol. Immunol.*, 39(15):941-52 (2003).
Chien et al., "Significant structural and functional change of an antigen-binding site by a distant amino acid substitution: proposal of a structural mechanism," *Proc. Natl. Acad. Sci. USA*, 86(14):5532-5536 (1989).
Ishiguro et al., "Anti-glypican 3 antibody as a potential antitumor agent for human liver cancer," *Cancer Res.*, 68(23):9832-8 (2008).
Noda et al., "Relationship between elevated FX expression and increased production of GDP-L-fucose, a common donor substrate for fucosylation in human hepatocellular carcinoma and hepatoma cell lines," *Cancer Res.*, 63:6282-6289 (2003).
Shuo et al., "The Antitumor Effects of Anti-CD71 Mouse/Human Chimeric Antibody in vitro," *J Huazhong Univ Sci Tech* (Health Sci), 32(1):13 (Feb. 2003) (including English abstract).
Winkler et al., "Changing the antigen binding specificity by single point mutations of an anti-p24 (HIV-1) antibody," *J. Immunol.*, 165(8):4505-4514 (2000).
USPTO Final Office Action in U.S. Appl. No. 11/251,561, dated Sep. 25, 2013, 16 pages.
Fish & Richardson P.C., Reply to Final Office Action dated Sep. 25, 2013 in U.S. Appl. No. 11/251,561, filed Feb. 25, 2014, 29 pages.
USPTO Non-Final OA in U.S. Appl. No. 12/852,950, dated Oct. 4, 2013, 34 pages.
Office Action for Chinese App. Ser. No. 201210178007.3, dated Sep. 29, 2013, 8 pages.
Office Action for Taiwanese App. Ser. No. 094137496, dated Dec. 31, 2010, 8 pages.
Office Action for Costa Rica App. Ser. No. 9151, dated Feb. 18, 2013 (with English translation), 15 pages.
USPTO Final Office Action in U.S. Appl. No. 12/797,349, dated Dec. 11, 2013, 6 pages.
Declaration of Pamela J. Bjorkman under 37 C.F.R. § 1.132, dated Jan. 17, 2011, 14 pages.
Dipiro et al., "Lesson 2: Basic Pharmacokinetics," Concept in Clinical Pharmacokinetics, Fifth Edition, American Society of Health-System Pharmacists, pp. 19-28 (2010).
Wang et al., "Monoclonal Antibody Pharmacokinetics and Pharmacodynamics," *Clinical Pharmacology & Therapeutics*, 84(5):548-558 (2008).
Fish & Richardson P.C., Amendment in Reply to Action dated Oct. 4, 2013 in U.S. Appl. No. 12/852,950, filed Apr. 3, 2014, 49 pages.
USPTO Non-Final Office Action in U.S. Appl. No. 11/251,561, dated Apr. 4, 2014, 18 pages.
USPTO Final Office Action in U.S. Appl. No. 12/852,950, dated Jul. 16, 2014, 38 pages.
Fish & Richardson P.C., Reply to Final Office Action dated Dec. 11, 2013, in U.S. Appl. No. 12/797,349, filed Jan. 9, 2015, 6 pages.

* cited by examiner

ANTI-GLYPICAN-3 ANTIBODY

CROSS-REFERENCE TO RELATED APPLICATIONS

This application is the National Stage of international Application Serial No. PCT/US2006/039682, filed on Oct. 11, 2006, which is a continuation of and claims the benefit of U.S. application Ser. No. 11/251,561, filed on Oct. 14, 2005. The contents of both of the foregoing applications are hereby incorporated by reference in their entirety.

TECHNICAL FIELD

The present invention relates to an anti-glypican-3 antibody. Specifically, the present invention relates to an anti-glypican-3 antibody which has modifications in the amino acid sequence of the Fc region and exhibits enhanced ADCC activity.

BACKGROUND

Glypican-3 (GPC3) is one of a heparan sulfate proteoglycan family existing on the surface of cells, and it is suggested that GPC3 may participate in cell division in development and in growth of cancer cells, but its function is not as yet well clarified.

It has been found that a certain antibody binding to GPC3 has a cell growth-inhibiting effect through its ADCC (antibody-dependent cytotoxicity) activity and CDC (complement-dependent cytotoxicity) (WO2003/000883, hereby incorporated by reference in its entirety).

In the case where an anticancer agent utilizing the cytotoxicity activity of an antibody is developed, it is desirable that the antibody to be used has enhanced ADCC activity. Thus, an anti-GPC3 antibody having enhanced cytotoxicity activity is desired for the GPC3-recognizing antibody.

An object of the invention is to provide an anti-GPC3 antibody having enhanced cytotoxicity as compared with conventional antibodies.

SUMMARY

It was found that an anti-glypican-3 antibody with enhanced ADCC activity may be obtained by modifying the amino acid sequence in the Fc region of the antibody.

In one aspect, the present invention provides an anti-glypican-3 antibody comprising one or more amino acid substitutions introduced in the Fc region.

In another aspect, the present invention provides an anti-glypican-3 antibody in which one or more of the amino acid residues at the positions 239, 298, 326, 330 and 332 in the Fc region are substituted with other amino acid residues.

In another aspect, the present invention provides an anti-glypican-3 antibody selected from the group consisting of:
  (a) an anti-glypican-3 antibody in which the amino acid residue at the position 332 of the Fc region is substituted with another amino acid residue;
  (b) an anti-glypican-3 antibody in which the amino acid residues at the positions 239, 330 and 332 of the Fc region are substituted with other amino acid residues;
  (c) an anti-glypican-3 antibody in which the amino acid residues at the positions 239, 298 and 332 of the Fc region are substituted with other amino acid residues;
  (d) an anti-glypican-3 antibody in which the amino acid residues at the positions 239, 326 and 332 of the Fc region are substituted with other amino acid residues;
  (e) an anti-glypican-3 antibody in which the amino acid residues at the positions 239, 298, 326 and 332 of the Fc region are substituted with other amino acid residues.

In another aspect, the present invention provides an anti-glypican-3 antibody selected from the group consisting of:
  (a) an anti-glypican-3 antibody having glutamic acid at the position 332 of the Fc region;
  (b) an anti-glypican-3 antibody having aspartic acid at the position 239, leucine at the position 330, and glutamic acid at the position 332 of the Fc region;
  (c) an anti-glypican-3 antibody having aspartic acid at the position 239, alanine at the position 298, and glutamic acid at the position 332 of the Fc region;
  (d) an anti-glypican-3 antibody having aspartic acid at the position 239, threonine at the position 326, and glutamic acid at the position 332 of the Fc region;
  (e) an anti-glypican-3 antibody having aspartic acid at the position 239, alanine at the position 298, glutamic acid at the position 326, and glutamic acid at the position 332 of the Fc region.

In another aspect, the present invention provides an anti-glypican-3 antibody selected from the group consisting of:
  (a) an anti-glypican-3 antibody in which the amino acid residue at the position 332 of the Fc region is substituted with glutamic acid;
  (b) an anti-glypican-3 antibody in which the amino acid residues at the positions 239, 330 and 332 of the Fc region are substituted with aspartic acid, leucine, and glutamic acid, respectively;
  (c) an anti-glypican-3 antibody in which the amino acid residues at the positions 239, 298 and 332 of the Fc region are substituted with aspartic acid, alanine, and glutamic acid, respectively;
  (d) an anti-glypican-3 antibody in which the amino acid residues at the positions 239, 326 and 332 of the Fc region are substituted with aspartic acid, threonine, and glutamic acid, respectively;
  (e) an anti-glypican-3 antibody in which the amino acid residues at the positions 239, 298, 326 and 332 of the Fc region are substituted with aspartic acid, alanine, glutamic acid, and glutamic acid, respectively.

In another aspect, the present invention provides an anticancer agent comprising the anti-glypican-3 antibody of the invention and a pharmaceutically acceptable carrier, as well as a method of treating a patient with cancer comprising administering to the patient the anticancer agent of the invention.

In another aspect, the present invention provides a method for producing an anti-glypican-3 antibody with enhanced cytotoxicity comprising:
  (i) culturing a host cell engineered to express a polynucleotide coding for an anti-glypican-3 antibody in which one or more of the amino acid residues at the positions 239, 298, 326, 330 and 332 of the Fc region are substituted by other amino acid residues; and
  (ii) isolating the antibody from the culture.

In another aspect, the present invention provides a method for producing an anti-glypican-3 antibody with enhanced cytotoxicity comprising:
  (i) culturing a host cell engineered to express a polynucleotide coding for an anti-glypican-3 antibody selected from the group consisting of:
    (a) an anti-glypican-3 antibody in which the amino acid residue at the position 332 of the Fc region is substituted with another amino acid residue;

(b) an anti-glypican-3 antibody in which the amino acid residues at the positions 239, 330 and 332 of the Fc region are substituted with other amino acid residues;

(c) an anti-glypican-3 antibody in which the amino acid residues at the positions 239, 298 and 332 of the Fc region are substituted with other amino acid residues;

(d) an anti-glypican-3 antibody in which the amino acid residues at the positions 239, 326 and 332 of the Fc region are substituted with other amino acid residues;

(e) an anti-glypican-3 antibody in which the amino acid residues at the positions 239, 298, 326 and 332 of the Fc region are substituted with other amino acid residues; and (ii) isolating the antibody from the culture.

In another aspect, the present invention provides a method for producing an anti-glypican-3 antibody with enhanced cytotoxicity comprising:

(i) culturing a host cell engineered to express a polynucleotide coding for an anti-glypican-3 antibody selected from the group consisting of:

(a) an anti-glypican-3 antibody having glutamic acid at the position 332 of the Fc region;

(b) an anti-glypican-3 antibody having aspartic acid at the position 239, leucine at the position 330, and glutamic acid at the position 332 of the Fc region;

(c) an anti-glypican-3 antibody aspartic acid at the position 239, alanine at the position 298, and glutamic acid at the position 332 of the Fc region;

(d) an anti-glypican-3 antibody having aspartic acid at the position 239, threonine at the position 326, and glutamic acid at the position 332 of the Fc region;

(e) an anti-glypican-3 antibody having aspartic acid at the position 239, alanine at the position 298, glutamic acid at the position 326, and glutamic acid at the position 332 of the Fc region; and (ii) isolating the antibody from the culture.

In still another aspect, the present invention provides an anti-glypican-3 antibody selected from the group consisting of:

(a) an anti-glypican-3 antibody having the CH2-CH3 domain comprising the amino acid sequence set forth in SEQ ID NO: 34;

(b) an anti-glypican-3 antibody having the CH2-CH3 domain comprising the amino acid sequence set forth in SEQ ID NO: 35;

(c) an anti-glypican-3 antibody having the CH2-CH3 domain comprising the amino acid sequence set forth in SEQ ID NO: 36;

(d) an anti-glypican-3 antibody having the CH2-CH3 domain comprising the amino acid sequence set forth in SEQ ID NO: 37; and (e) an anti-glypican-3 antibody having the CH2-CH3 domain comprising the amino acid sequence set forth in SEQ ID NO: 38.

DETAILED DESCRIPTION

Figure 1:
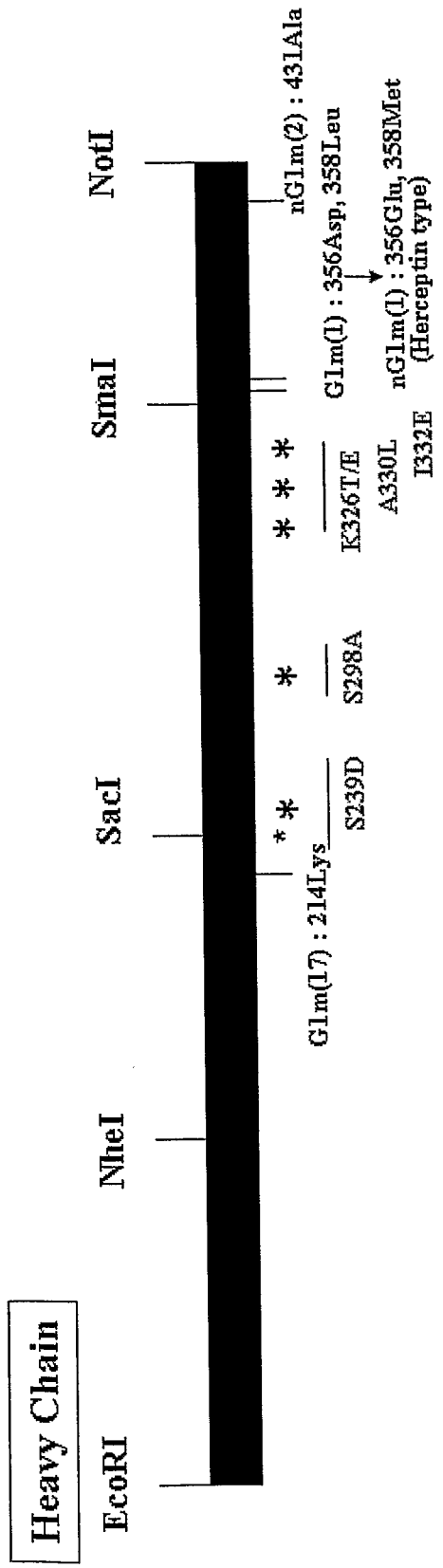
FIG. 1 shows the scheme for preparing the Fc-modified humanized anti-glypican-3 antibody of the invention.

The present invention provides an antibody having modifications in the Fc region. FIG. 1 shows the structure and preparation scheme of the Fc-modified humanized anti-glypican-3 antibody of the invention.

In general, the antibody is a heterotetramer of about 150,000 daltons, and comprises two same light (L) chains and two same heavy (H) chains. Each light chain is bound to the heavy chain via one covalent disulfide bond, and the number of the disulfide bonds between the heavy chains varies depending on the isotype of antibody. The heavy chain and the light chain each have intra-chain disulfide bridges at certain intervals. Each heavy chain has a variable domain (VH) at one terminal thereof, and has many constant domains linked thereto. Each light chain has a variable domain (VL) at one terminal thereof and has a constant region at the other terminal thereof. The constant region of the light chain is in parallel to the first constant region of the heavy chain, and the variable region of the light chain is in parallel to the variable region of the heavy chain. It is believed that specific amino acid residues form an interface of the variable domain of the light chain and the heavy chain (Clothia et al., J. Mol. Biol., 186: 651-666 (1985); Novotny and Haber, Proc. Natl. Acad. Sci. USA 82:4592-4596 (1985), all hereby incorporated by reference in its entirety).

The light chain of a vertebrate-derived antibody may be classified into two different types, referred to as kappa (κ) and lambda (λ), based on the amino acid sequence of the constant region thereof. In addition, the antibody may be classified into different classes based on the amino acid sequence of the constant domain of the heavy chain thereof. The antibody includes at least five main classes: IgA, IgD, IgE, IgG and IgM, and some of them may be classified into subclasses (isotypes), e.g., IgG-1, IgG-2, IgG-3 and IgG-4; IgA-1 and IgA-2. The heavy chain constant domains of different classes are referred to as α, δ, ε, γ and μ. The subunit structure and the three-dimensional structure of immunoglobulin of each class are known in the art. It is also known that there exist allotypes in the sequence of the Fc region of IgG-1, for example, Glm(1), nGlm(1), Glm(2), Glm(3), nGlm(17), etc. (M. S. Schanfield and E. van Loghem, "Human Immunoglobulin Allotypes" Handbook of Experimental Immunology, Vol. 3, ch 94, pp 1-18, Blackwell Scientific Publishers. Oxford, U.K. 1986, 4th Edition, hereby incorporated by reference in its entirety).

Fc region means a region of an Fc fragment of an antibody molecule, comprising a part of hinge, CH2 and CH3 domains and having a molecular weight of about 50,000. A human IgG heavy chain Fc region is from the 225th threonine to the C-terminal, in the case that the molecule is digested with papain (Burton, D. R. 1985. Immunoglobulin G: functional sites. Mol. Immunol. 22:161-206, hereby incorporated by reference in its entirety).

The numbering of the amino acid position as used herein refers to the method of "EU index" by Kabat et al (Kabat E A et al., 1991, Sequence of Proteins of Immunological Interest. 5th Ed. NIH, hereby incorporated by reference in its entirety).

The Fc region binds to an Fc receptor (FcR) present on the cell surface of effector cells, such as macrophages and NK cells. The Fc receptor participates in antibody-dependent cytotoxicity (ADCC), anaphylaxis reaction, id reaction, etc. The type of Fc receptor varies, depending on the subtype of immunoglobulin. For example, Fc receptor of IgG is Fcγ receptor; Fc receptor of IgE is Fcε receptor; and Fc receptor of IgA is Fcα receptor.

The CH2-CH3 domain consists of the CH2 domain and the CH3 domain. The CH2-CH3 domain of a human IgG heavy chain is from the 233th alanine to the C-terminal.

Fc-Modified Antibody

The antibody of the invention is an Fc-modified antibody in which the amino acid sequence in the Fc region is modified. "Modification" or "site-specific mutagenesis (mutagenesis)" used in the invention includes substituting an original (unmodified) amino acid residue with any other amino acid residue, deletion of an original amino acid residue, and addition of an additional amino acid residue, but preferably indicates substitution of an original amino acid residue with any other amino acid residue. The original (unmodified) amino acid sequence as referred to herein is usually a natural Fc region sequence. In this context, "modification" and "mutagenesis" of amino acid residue are used in the same meaning.

In the invention, modification of amino acid residues may be effected by mutating the DNA that codes for the antibody.

In the invention, "mutation of DNA" means that DNA is mutated in such a manner that it may correspond to the amino acid residue to be modified. More specifically, it means that the DNA coding for the original amino acid residue is mutated to DNA coding for the amino acid residue to be modified. In general, it means genetic engineering or mutagenesis treatment for insertion, deletion or substitution of at least one nucleotide of the original DNA so as to give a codon that codes for the intended amino acid residue. Specifically, the codon that codes for the original amino acid residue is substituted with the codon that codes for the amino acid residue to be modified. Those skilled in the art may easily carry out such a DNA mutation according to a known technique, for example, according to a site-specific mutagenesis method such as PCR mutagenesis method (Hashimoto-Gogoh, T. et al., (1995) Gene 152, 271-275; Zoller, M J, and Smith, M., (1983) Methods Enzymol., 100, 468-500; Kramer, W. et al., (1984) Nucleic Acids, Res., 12, 9441-9456; Kramer W. and Fritz H J, (1987) Methods Enzymol., 154, 350-367; Kunkel, T A, (1985) Proc. Natl. Acad. Sci. USA, 82, 488-492; Kunkel, (1988) Methods Enzymol., 85, 2763-2766, all hereby incorporated by reference in its entirety).

The number of the amino acid residues in the Fc region to be modified in the invention is not specifically limited, but one or more (for example, from 1 to 30, or 2, 3, 4 or 5) amino acid residues may be modified.

Preferably, one or more of the amino acid residues at the positions 239, 298, 326, 330 and 332 in the Fc region are substituted with other amino acid residues. In addition, any amino acid residues of the Fc region may be substituted with those of any allotypes of IgG1, for example, with the amino acid residues of Glm(1) and nGlm(1).

The anti-glypican-3 antibody of the invention is not specifically limited so far as it binds to glypican-3, but preferably, the antibody specifically binds to glypican-3. The gene sequence and the amino acid sequence of glypican-3 are known (Lage, H. et al., Gene 188 (1997), 151-156, hereby incorporated by reference in its entirety). The anti-glypican-3 antibody of the invention is preferably IgG, more preferably Igb1.

Cytotoxicity

The anti-glypican-3 antibody of the invention containing modified Fc region exhibits enhanced cytotoxicity activity as compared with the anti-glypican-3 antibody having a natural or wild type Fc region.

Cytotoxicity activity includes, for example, antibody-dependent cell-mediated cytotoxicity (ADCC) activity, and complement-dependent cytotoxicity (CDC) activity. In the invention, the CDC activity means a cytotoxicity activity caused by a complement system; and the ADCC activity means that, when a specific antibody adheres to the cell surface antigen of a target cell, then an Fcγ receptor-having cell (e.g., immunocyte) binds to the Fc region via an Fcγ receptor to thereby impair the target cell.

Determination of whether an antibody has ADCC activity or CDC activity may be carried out according to a known method (for example, see Current Protocols in Immunology, Chapter 7, Immunologic Studies in Humans, Editor, John E. Coligan et al., John Wiley & Sons, Inc. (1993), hereby incorporated by reference in its entirety).

For example, the ADCC activity may be determined by mixing an effector cell, a target cell and an anti-glypican-3 antibody, then analyzing it for the degree of ADCC activity. The effector cell may include, for example, a mouse spleen cell, or a monocyte isolated from marrow or human peripheral blood. The target cell may include an established human cell line such as human hepatocyte cell line HuH-7. An anti-glypican-3 antibody is added to the target cell previously labeled with 51Cr and incubated, then an effector cell is added in a suitable ratio to the target cell. After incubation, the supernatant is collected and analyzed for radioactivity to determine the ADCC activity of the antibody.

The CDC activity may be determined by mixing the above-mentioned labeled target cell and an anti-glypican-3 antibody, adding a complement to the mixture and incubating, and then analyzing the supernatant for radioactivity.

Antibody

The term "antibody" as referred to herein is used in the broadest sense of the word, indicating any and every antibody that includes monoclonal antibody (including full-length monoclonal antibody), polyclonal antibody, antibody mutant, antibody fragment, poly-specific antibody (e.g., bispecific antibody), chimera antibody, humanized antibody and others, so far as it shows the desired biological activity.

Antibody and immunoglobulin are proteins having the same structure characteristics, and the antibody in the invention includes immunoglobulin.

The term "monoclonal antibody" as referred to herein indicates an antibody obtained from a group of substantially homogeneous antibodies, or that is, an antibody group in which all individual antibodies are uniform except minor mutants that may occur in nature. A monoclonal antibody is highly specific and generally acts on a single antigen site. Further, as compared with conventional polyclonal antibody preparations that typically include different antibodies to different epitopes, each monoclonal antibody is directed to a single epitope on an antigen. In addition to the specificity thereof, a monoclonal antibody has another advantage in that it is synthesized through culture of a hybridoma which is not contaminated with any other antibodies. The modifier "monoclonal" suggests the nature of the antibody obtained from a group of substantially uniform antibodies, and it does not require that the antibody be produced by a specific method. For example, the monoclonal antibody for use in the invention may be produced, for example, according to a hybridoma method (Kohler and Milstein, Nature 256:495 (1975), hereby incorporated by reference in its entirety), or a recombination method (U.S. Pat. No. 4,816,567, hereby incorporated by reference in its entirety). The monoclonal antibody for use in the invention may also be isolated from a phage antibody library (Clackson et al., Nature 352:624-628 (1991); Marks et al., J. Mol. Biol., 222:581-597 (1991), all hereby incorporated by reference in its entirety).

The term "antibody fragment" indicates a portion of a full-length antibody. The antibody fragment for use in the invention is preferably an antibody fragment that maintains an antibody-binding activity and maintains a cytotoxicity activity of the full-length antibody.

A multi-specific antibody is an antibody having specificity to at least two different antigens. In general, this type of molecule may bind to two antigens (that is, bispecific antibody), but in this description, the "multi-specific antibody" includes antibodies having specificity to more than two (for example, three) antigens. The multi-specific antibody may be a full-length antibody or a fragment of such an antibody. For example, the bispecific antibody may recognize two different antigens or may recognize different epitopes of one antigen. In addition, one may recognize a cytotoxic substance.

The antibody of the present invention may also be a chimera antibody or a humanized antibody. In general, a chimera antibody comprises a variable region derived from an antibody of a non-human mammal, and a constant region derived from a human antibody. On the other hand, humanized antibody comprises a complementarity-determining region derived from a non-human mammal, and a framework region and a constant region derived from a human antibody.

The origin of the variable region in a chimera antibody, and the origin of a CDR in a humanized antibody are not specifically limited, but may be derived from any animals. For example, any sequences derived from mouse antibody, rat antibody, rabbit antibody, or camel antibody may be used (Cook W J et al., Protein Eng. Jul. 9, 1996 (7):623-8; Tsurushita N et al., J Immunol Methods. 2004 December 295(1-2):9-19; Sato K et al, Mol Immunol. Apr. 31, 1994 (5):371-81; Preparation of genetically engineered monoclonal antibodies for human immunotherapy. Hum Antibodies Hybridomas. Jul. 3, 1992 (3):137-45; Genetically engineered antibodies: progress and prospects. Crit Rev Immunol. 1992; 12(3-4): 125-68, all hereby incorporated by reference in its entirety).

For the constant region of a chimera antibody and a humanized antibody, those derived from a human antibody may be used. For example, Cγ1, Cγ2, Cγ3, Cγ4 may be used for the H-chain, and Cκ and Cλ may be used for the L-chain.

Chimera antibody is an antibody constructed by combining sequences derived from different animals, and for example, it is an antibody comprising the heavy chain and light chain variable regions of a mouse antibody and the heavy chain and light chain constant regions of a human antibody. Such a chimera antibody may be constructed in any known methods. For example, a DNA coding for a mouse antibody variable region and a DNA coding for a human antibody constant region are ligated, then inserted into an expression vector, and introduced into a host to produce the intended antibody.

A humanized antibody, also referred to as a reshaped human antibody, is constructed by transplanting a complementarity-determining region (CDR) of an antibody of a mammal except human, for example, a mouse antibody into the complementarity-determining region of a human antibody. A general genetic recombination method for making a humanized antibody is known in the art (see EP 125023; WO96/02576, hereby incorporated by reference in its entirety).

Specifically, a DNA sequence designed so as to ligate CDR of a mouse antibody with the framework region (FR) of a human antibody may be synthesized through PCR using, as a primer, several oligonucleotides constructed so as to have portions overlapping with the terminal region of both CDR and FR (see the method described in WO98/13388, hereby incorporated by reference in its entirety).

The framework region of a human antibody to be ligated with CDR is so selected that the complementarity-determining region may form a good antigen-binding site. If desired, the amino acids in the framework region of the variable region of the antibody may be substituted in order that the complementarity-determining region of the reshaped human antibody may form a suitable antigen-binding site (Sato, K. et al., Cancer Res. (1993) 53, 851-856, hereby incorporated by reference in its entirety).

In addition, those antibodies are also included in the antibody of the invention which have mutation in one or more amino acids in regions other than the specified sites in the Fc region mentioned above or CDR region, and which is functionally equivalent to the antibody of the invention.

For preparing a polypeptide that comprises a different amino acid sequence but is functionally equivalent to a certain polypeptide, a method of introducing a mutation into the polypeptide is well known to those skilled in the art. For example, those skilled in the art may introduce a mutation to the antibody of the invention according to a site-specific mutagenesis or the like to thereby prepare an antibody functionally equivalent to that antibody. Amino acid mutation may also occur spontaneously.

Preferably, an amino acid residue is mutated to another amino acid residue which has side chain properties close to that of the original one. For example, regarding the properties thereof, amino acid side chains include hydrophobic amino acids (A, I, L, M, F, P, W, Y, V), hydrophilic amino acids (R, D, N, C, E, Q, G, H, K, S, T), aliphatic side chain-having amino acids (G, A, V, L, I, P), hydroxyl group-containing side chain-having amino acids (S, T, Y), sulfur atom-containing side chain-having amino acids (C, M), carboxylic acid and amido-containing side chain-having amino acids (D, N, E, Q), base-containing side chain-having amino acids (R, K, H), aromatic side chain-having amino acids (H, F, Y, W) (the parenthesized alphabets are the one-letter code for amino acids). It is known that a polypeptide having an amino acid sequence modified from the original amino acid sequence through deletion, addition and/or substitution with any other amino acid of one or more amino acid residues therein still substantially maintain the biological activity of the original polypeptide (Mark, D. F. et al., Proc. Natl. Acad. Sci. USA (1984) 81, 5662-5666; Zoller, M. J. & Smith, M., Nucleic Acids Research (1982) 10, 6487-6500; Wang, A. et al., Science 224, 1431-1433; Dalbadie-McFarland, G., et al., Proc. Natl. Acad. Sci. USA (1982) 79, 6409-6413, all hereby incorporated by reference in its entirety).

The antibody for use in the invention may be a conjugated antibody bound with a various types of molecules, such as non-peptidic polymers such as polyethylene glycol (PEG), radioactive substances and toxins. Such a conjugated antibody may be obtained through chemical modification of the antibody. The method of chemical modification has been established in the art. The antibody of the invention may include these conjugated antibodies (D. J. King., Applications and Engineering of Monoclonal antibodies., 1998 T.J. International Ltd, Monoclonal Antibody-Based Therapy of Cancer., 1998 Marcel Dekker Inc; Chari et al., Cancer Res., 1992 Vol 152:127; Liu et al., Proc Natl Acad Sci USA., 1996 Vol 93:8681, all hereby incorporated by reference in its entirety).

Antibody Preparation

The antibody of the invention may be produced according to a method known to those skilled in the art. Specifically, DNA coding for the intended antibody is inserted into an expression vector. In this step, DNA is inserted into an expression vector in such a manner that it could be expressed under control of an expression control region, for example, an enhancer and a promoter. Next, a host cell is transformed with the expression vector and the antibody is expressed in the host cell. In this process, a combination of a suitable host and a suitable expression vector may be used.

Examples of the vector include M13 vector, pUC vector, pBR322, pBluescript, pCR-Script. For subcloning and separation of cDNA, for example, pGEM-T, pDIRECT and pT7 may also be used.

Expression vectors are especially useful for the purpose of antibody production. When *E. coli* such as JM109, DH5α, HB101 or XL1-Blue is used as a host, the expression vector must indispensably have a promoter that drives efficient expression of the vector in *E. coli*, for example, lacZ promoter (Ward et al., Nature (1989) 341, 544-546; FASEB J. (1992) 6, 2422-2427, hereby incorporated by reference in its entirety), araB promoter (Better et al., Science (1988) 240, 1041-1043, hereby incorporated by reference in its entirety) or T7 promoter. The vector of this type also includes pGEX-5X-1 (Pharmacia), QIA express system (QIAGEN), pEGFP, and pET (in this case, the host is preferably a T7 RNA polymerase-expressing BL21).

The vector may include a signal sequence for polypeptide secretion. For the signal sequence for polypeptide secretion, for example, pelB signal sequence (Lei, S. P. et al., Bacteriol. (1987) 169, 4397, hereby incorporated by reference in its entirety) may be used for production in periplasm of *E. coli*. The introduction of the vector into a host cell may be effected, for example, according to a calcium chloride method or an electroporation method.

In addition to the *E. coli* expression vectors, the vector used for polypeptide production in the invention includes, for example, mammal-derived expression vectors (e.g., pcDNA3 (Invitrogen), pEGF-BOS (Nucleic acids, Res., 1990, 18(17), p. 5322, hereby incorporated by reference in its entirety), pEF, pCDM8); insect cell-derived expression vectors (e.g., Bac-toBAC baculovairus expression system (GIBCO BRL), pBacPAK8); vegetable-derived expression vectors (e.g., pMH1, pMH2); animal virus-derived expression vectors (e.g., pHSV, pMV, pAdexLcw), retrovirus-derived expression vectors (e.g., pZIPneo), yeast-derived expression vectors (e.g., *Pichia* Expression Kit (Invitrogen), pNV11, SP-Q01), *Bacillus subtilis*-derived expression vectors (e.g., pPL608, pKTH50).

For expression in animal cells such as CHO cells, COS cells or NIH3T3 cells, the vector must indispensably have a promoter necessary for intracellular expression, for example, SV40 promoter (Mulligan et al., Nature (1979) 277, 108, hereby incorporated by reference in its entirety), MMTV-LTR promoter, EF1α promoter (Mizushima et al., Nucleic Acids Res. (1990) 18, 5322, hereby incorporated by reference in its entirety), CAG promoter (Gene (1991) 108, 193, hereby incorporated by reference in its entirety), CMV promoter. Preferably, the vector has a gene for screening of the transformed cells (e.g., drug-resistant gene capable of being differentiated by drug (e.g., neomycin, G418)). The vector having such characteristics includes, for example, pMAM, pDR2, pBK-RSV, pBK-CMV, pOPRSV, pOP13.

Further, for the purpose of stable gene expression and an increase in the number of gene copies in cells, a vector having a complementary DHFR gene (e.g., pCHOI) is introduced into CHO cells deficient in the nucleic acid synthetic pathway to complement the deficiency and is amplified with methotrexate (MTX). For the purpose of transient expression of the gene, COS cells having an SV40T antigen-expressing gene on the chromosome is transformed with a vector having SV40 replication origin (e.g., pcD). The replication origin may also be derived from polyoma virus, adenoma virus, bovine polyoma virus (BPV), etc. Further, for increasing the number of gene copies in a host cell system, the expression vector may contain a selected marker, such as aminoglycoside transferase (APH) gene, thymidine kinase (TK) gene, *E. coli* xanthine-guanine phosphoribosyl transferase (Ecogpt) gene, dihydrofolate reductase (dhfr) gene.

Pharmaceutical Composition

The invention also relates to a pharmaceutical composition containing the antibody of the invention. Since the antibody of the invention exhibits enhanced cytotoxicity activity, it is suitable for use in pharmaceutical compositions, and in particular, it is useful as an anticancer agent. Since it has been shown that an anti-glypican-3 antibody has a cytotoxicity against a hepatoma-derived cell line (e.g. WO03/00883, hereby incorporated by reference in its entirety), the antibody of the invention is particularly useful as a drug for treating hepatic cancer. When the antibody of the invention is used in pharmaceutical compositions, it is preferably a humanized antibody in view of the antigenicity to humans.

The pharmaceutical composition of the invention may contain a pharmaceutically-acceptable carrier. The pharmaceutically-acceptable carrier includes, for example, sterile water, physiological saline, stabilizer, excipient, antioxidant (e.g., ascorbic acid), buffer (e.g., phosphoric acid, citric acid, other organic acids), preservative, surfactant (e.g., PEG, Tween), chelating agent (e.g., EDTA), or binder. In addition, the pharmaceutical composition of the invention may further contain any other low-molecular polypeptides; proteins such as serum albumin, gelatin, or immunoglobulin; amino acids such as glycine, glutamine, asparagine, arginine, lysine; saccharides such as polysaccharides, monosaccharides; carbohydrates; sugar alcohols such as mannitol, sorbitol. When the composition is prepared as an aqueous solution for injection, it may be combined with an isotonic solution containing, for example, physiological saline, glucose or any other auxiliary agent, such as D-sorbitol, D-mannose, D-mannitol, sodium chloride, and with a suitable dissolution aid such as alcohol (e.g., ethanol), polyalcohol (e.g., propylene glycol, PEG), nonionic surfactant (e.g., Polysorbate 80, HCO-50).

If desired, the composition may be encapsulated into microcapsules (microcapsules of hydroxymethyl cellulose, gelatin, poly(methyl methacrylate), etc.), or may be formed into colloid drug delivery systems (e.g., liposomes, albumin microspheres, microemulsions, nanoparticles, nanocapsules) (see Remington's Pharmaceutical Science, 16th edition, Oslo Ed., 1980, hereby incorporated by reference in its entirety). Further, a method of formulating slow-release drugs is known and may be applicable to the invention (Langer et al., J. Biomed. Mater. Res., 1981, 15:167-277; Langer, Chem. Tech., 1982, 12:98-105; U.S. Pat. No. 3,773,919; EP 58,481; Sidman et al., Biopolymers 1983, 22:547-556; EP 133,988).

The composition may be administered to patients either orally or parenterally, but preferably parenterally. The shape (preparation form) of the pharmaceutical composition of the invention is not specifically limited but includes, for example, injections, transnasal preparations, transpulmonary preparations, percutaneous preparations, freeze-dried preparations, solutions. Preferred are freeze-dried preparations.

Freeze-drying may be effected in any method well known to those skilled in the art (Pharm. Biotechnol., 2002, 13, 109-133; Int. J. Pharm., 2000, 203(1-2), 1-60; Pharm. Res., 1997, 14(8), 969-975, all hereby incorporated by reference in its entirety). For example, a solution of the composition is suitably aliquoted into freeze-drying vials or the like vessels, and put in a freezer or a freeze-dryer, or dipped in a coolant such as acetone/dry ice and liquid nitrogen. When the antibody preparation is formed into a high-concentration solution preparation, it may be prepared according to a method well known to those skilled in the art. For example, a membrane concentration method using a TFF membrane may be employed as described in J. Pharm. Sci., 2004, 93(6), 1390-1402, hereby incorporated by reference in its entirety.

The formulation for injection may be systemically or topically administered in a mode of, for example, intravenous injection, intramuscular injection, intraperitoneal injection or subcutaneous injection. Depending on the age and the condition of the patient to which the composition is administered, the administration method for it may be suitably selected. The dose may be selected, for example, from a range of from 0.0001 mg/kg of body weight to 1000 mg/kg of body weight for a unit dose. Alternatively, the dose may be selected from a range of from 0.001 to 100000 mg/body. However, the invention should not be limited to the dose and the administration method as above.

The invention is described in more detail with reference to the following Examples, to which, however, the invention should not be limited.

EXAMPLES

Example 1

Production of Fc-Modified Anti-GPC3 Antibody

Example 1-1

Preparation of Fc Cassettes for Mutagenesis

Fc-modified humanized anti-GPC3 antibodies having amino acid substitutions shown in the table below in the amino acid sequence of the H-chain shown in SEQ ID NO: 19. FIG. 1 shows the structure and preparation strategy of the Fc-modified antibodies of the invention.

| | |
|---|---|
| V22 | I332E |
| V209 | S239D/A330L/I332E |
| V212 | S239D/S298A/I332E |
| V922 | S239D/K326T/I332E |
| V1608 | S239D/S298A/K326E/I332E |
| V209nG1m(1) | S239D/A330L/I332E/D356E/L358M |

Using primers shown by SEQ ID NO:1 to NO:9, Fc-mutation cassettes for constructing five types of Fc-modified antibodies named V22, V209, V212, V922 and V1608 were produced according to a PCR-Walking method. Specifically, primers commonF1 and commonR1 were used for V22, V209 and V922; and primers 212-F1 and 212-F1 were used for V212 and V1608. A first-stage PCR was carried out in a PCR reaction solution mentioned below:

x10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), dH$_2$O 35.5 µl, and 5 units/l KOD polymerase 0.5 µl were added to make 50 µl in total. PCR was carried out under the condition mentioned below.

96° C. 1 min; (98° C. 15 sec; 65° C. 2 sec; 74° C. 15 sec)×2 cycles; 74° C. 30 sec; 4° C.

One microliter of the first stage-amplified product was taken out and used in the next, second-stage PCR reaction. Specifically, primers CommonF2 and 212-R2 were used for V22 and V212; primers CommonF2 and 209-R2 were used for V209; primers CommonF2 and 922-R2 were used for V922; and primers CommonF2 and 1608-R2 were used for V1608. The second-stage PCR was carried out in a PCR reaction solution mentioned below:

x10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), 1 µl of the first stage-amplified product as a template, dH$_2$O 35.5 µl, and 5 units/µl KOD polymerase 0.5 µl were added to make 51 µl in total. PCR was carried out under the condition mentioned below.

96° C. 1 min; (98° C. 15 sec; 65° C. 2 sec; 74° C. 15 sec)×5 cycles; 74° C. 30 sec; 4° C.

One microliter of the second stage-amplified product was taken out and used in the next, third-stage PCR reaction. Specifically, primers CommonF3 and CommonR3 were used for V22, V209, V212, V922 and V1608, and the third-stage PCR was carried out in a PCR reaction solution mentioned below.

x10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), 1 µl of the second stage-amplified product as a template, dH$_2$O 35.5 µl, and 5 units/µl KOD polymerase 0.5 µl were added to it to make 51 µl in total. Using this, PCR was carried out under the condition mentioned below.

96° C. 1 min; (98° C. 15 sec; 65° C. 2 sec; 74° C. 20 sec)×35 cycles; 74° C. 1 min; 4° C.

Each fragment obtained was subcloned into pBluescriptSK$^+$ and its sequence was confirmed.

```
Forward primer: 212-F1
                                        (SEQ ID NO: 1)
agttcaactggtacgtggacggcgtggaggtgcataatgccaagacaaag ccgcgggaggagcagtacaacgccacgtaccgtgtggtcagcgtcc Forward primer: commonF2
                                        (SEQ ID NO: 2)
tctcccggacccctgaggtcacatgcgtggtggtggacgtgagccacgaa gaccctgaggtcaagttcaactggtacgtggacggcgtggagg Forward primer: commonF3
                                        (SEQ ID NO: 3)
gcacctgagctcctgggggaccggacgtcttcctcttcccccaaaacc caaggacacctcatgatctcccggacccctgaggtcacatgcgtgg Reverse primer: 212-R1
                                        (SEQ ID NO: 4)
ggagaccttgcacttgtactccttgccattcagccagtcctggtgcagga cggtgaggacgctgaccacacggtacgtggcgttgtactgctcc Reverse primer: 209-R2
                                        (SEQ ID NO: 5)
ggctgcccttggctttggagatggttttctcctcgggcagtgggagggc tttgttggagaccttgcacttgtactccttgccattcagcc Reverse primer: 212-R2
                                        (SEQ ID NO: 6)
ggctgcccttggctttggagatggttttctcctcggggctgggagggc tttgttggagaccttgcacttgtactccttgccattcagcc
```

-continued

Reverse primer: 922-R2
(SEQ ID NO: 7)
ggctgccctttggctttggagatggttttctcctcgggggctgggagggc ggtgttggagaccttgcacttgtactccttgccattcagcc Reverse primer: 1608-R2
(SEQ ID NO: 8)
ggctgccctttggctttggagatggttttctcctcgggggctgggagggc ctcgttggagaccttgcacttgtactccttgccattcagcc Reverse primer: commonR3
(SEQ ID NO: 9)
gagctccccgggatgggggcagggtgtacacctgtggttctcggggctgc cctttggctttggagatggttttctcctcgg

Example 1-2

Preparation of Vector Expressing Fc-Modified Anti-GPC3 Antibody

A vector for expressing the Fc-modified anti-GPC3 antibody of the invention was constructed based on a gene coding for a humanized anti-glypican-3 antibody previously prepared by the inventors (H-chain, SEQ ID NO: 10; L-chain, SEQ ID NO: 11), which is referred to as "wild-type" in the following Examples.

The amino acid sequences of the H-chain variable region and L-chain variable region of the wild-type humanized anti-GPC3 antibody are shown in SEQ ID NO: 21 (ver.k) and SEQ ID NO: 22 (ver.a), respectively. The CDR sequences of the wild-type humanized anti-GPC3 antibody are shown below.

| H-chain | | |
|---|---|---|
| CDR1 | DYEMH | (SEQ ID NO: 23) |
| CDR2 | ALDPKTGDTAYSQKFKG | (SEQ ID NO: 24) |
| CDR3 | FYSYTY | (SEQ ID NO: 25) |
| L-chain | | |
| CDR1 | RSSQSLVHSNGNTYLH | (SEQ ID NO: 26) |
| CDR2 | KVSNRFS | (SEQ ID NO: 27) |
| CDR3 | SQNTHVPPT | (SEQ ID NO: 28) |

Using the anti-human GPC3 antibody H-chain gene shown by SEQ ID NO:10 as a template, and using a primer of SEQ ID NO:11 and a primer of SEQ ID NO:12 with a SacI site previously introduced as silent mutation, PCR was carried out under the condition mentioned below.

×10 KOD buffer 5 µl, dNTPs and MgCl$_2$ 5 µl and 2 µl, respectively, (attached to KOD polymerase, Toyobo) were mixed. The primer combination as above (20 µmole/l, 1 µl each), 1 µl of GPC3 antibody H-chain gene as a template, dH$_2$O 34.5 µl, and 5 units/µl KOD polymerase 0.5 µl were added to make 50 µl in total. PCR was carried out under the condition mentioned below.

96° C. 1 min; (98° C. 15 sec; 65° C. 2 sec; 74° C. 30 sec)×35 cycles; 74° C. 30 sec; 4° C.

The fragment obtained was introduced into the SmaI site of pBluescriptSK$^+$ (pB-Sacless), in which the SacI site had been previously filled up with a DNA blunting kit (Takara Bio), and its sequence was confirmed (pB-GPCSacmt). Next, from a vector containing an anti-GPC3 antibody H-chain gene shown by SEQ ID NO:10, an SmaI-BamHI fragment of about 290 bp, corresponding to the C-terminal sequence of anti-human GPC3 antibody H-chain, was cut out, and introduced into the corresponding site of pB-GPCSacmt (pB-GPCSacmtC). Next, the Fc-mutation cassette of V22, V209, V212, V922 or V1608 produced in Example 1-1 was introduced into the SacI-SmaI site of pB-GPCSacmtC, and the sequence of pB-GPCSacmtC was confirmed. Further, for completing construction of the mutated H-chain, an EcoRI-NheI fragment of about 415 bp of the GPC3 antibody H-chain gene shown by SEQ ID NO:10 was ligated with it to obtain a gene coding for Fc-mutated H-chain.

The resultant gene coding for a mutated H-chain was cleaved with EcoRI-NotI, and introduced into the corresponding site of an animal cell expression vector pCXND3 (pC-aGPCh). Next, a fragment of about 3.1 kb, containing an anti-GPC3 antibody L-chain gene shown by SEQ ID NO:13 and a promoter region, was cleaved with HindIII, and ligated with the corresponding site of pC-aGPCh to obtain an anti-GPC3 antibody expression vector (pC-aGPChl). The vector pC-aGPChl to V22, V209, V212, V922 and V1608 was designated as pC-aGPChl(22), pC-aGPChl(209), pC-aGPChl (212), pC-aGPChl(922) and pC-aGPChl(1608), respectively.

The amino acid sequence of the H chain of V22, V209, V212, V922 and V1608 are shown in V22 (SEQ ID NO: 29), V209 (SEQ ID NO: 30), V212 (SEQ ID NO: 31), V922 (SEQ ID NO: 32) and V1608 (SEQ ID NO: 33), respectively. The amino acid sequence of the CH2-CH3 domain of V22, V209, V212, V922 and V1608 are shown in V22 CH2-CH3 domain (SEQ ID NO: 34), V209 CH2-CH3 domain (SEQ ID NO: 35), V212 CH2-CH3 domain (SEQ ID NO: 36), V922 CH2-CH3 domain (SEQ ID NO: 37) and V1608 CH2-CH3 domain (SEQ ID NO: 38), respectively.

anti-human GPC3 antibody H-chain
(SEQ ID NO: 10)
GAATTCCACCATGGACTGGACCTGGAGGTTCCTCTTTGTGGTGGCAGCAG

CTACAGGTGTCCAGTCCCAGGTGCAGCTGGTGCAGTCTGGAGCTGAGGTG

AAGAAGCCTGGGGCCTCAGTGAAGGTCTCCTGCAAGGCTTCTGGATACAC

CTTCACCGACTATGAAATGCACTGGGTGCGACAGGCCCCTGGACAAGGGC

TTGAGTGGATGGGAGCTCTTGATCCTAAAACTGGTGATACTGCCTACAGT

CAGAAGTTCAAGGGCAGAGTCACGCTGACCGCGGACAAATCCACGAGCAC

AGCCTACATGGAGCTGAGCAGCCTGACATCTGAGGACACGGCCGTGTATT

ACTGTACAAGATTCTACTCCTATACTTACTGGGGCCAGGGAACCCTGGTC

ACCGTCTCCTCAGCTAGCACCAAGGGCCCATCGGTCTTCCCCCTGGCACC

CTCCTCCAAGAGCACCTCTGGGGGCACAGCGGCCCTGGGCTGCCTGGTCA

AGGACTACTTCCCCGAACCGGTGACGGTGTCGTGGAACTCAGGCGCCCTG

ACCAGCGGCGTGCACACCTTCCCGGCTGTCCTACAGTCCTCAGGACTCTA

CTCCCTCAGCAGCGTGGTGACCGTGCCCTCCAGCAGCTGGGCACCCAGAC

CTACATCTGCAACGTGAATCACAAGCCCAGCAACACCAAGGTGGACAAGA

AAGTTGAGCCCAAATCTTGTGACAAACTCACACATGCCCACCGTGCCCA

GCACCTGAACTCCTGGGGGACCGTCAGTCTTCCTCTTCCCCCCAAAACC

CAAGGACACCCTCATGATCTCCCGGACCCCTGAGGTCACATGCGTGGTGG

TGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGC

-continued

```
TGAATGGCAAGGAGTACAAGTGCAGGTCTCCAACAAAGCCCTCCCAGCCC

CCATCGAGAAAACCATCTCCAAAGCCAAAGGGCAGCCCCGAGAACCACAG

GTGTACACCCTGCCCCCATCCCGGGATGAGCTGACCAAGAACCAGGTCAG

CCTGACCTGCCTGGTCAAAGGCTTCTATCCCAGCGACATCGCCGTGGAGT

GGGAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGG

CTCTGCACAACCACTACACGCAGAAGAGCCTCTCCCTGTCTCCGGGTAAA

TGATAAGCGGCCGCGGATCC
```

Forward primer: NS-F (SEQ ID NO: 11)

```
gctagcaccaagggcccatcggtcttccccctggcacctcctcc
```

Reverse primer: NS-R (SEQ ID NO: 12)

```
gagctcaggtgctgggcacggtgggcatgtgtgagttttgtcac
``` anti-human GPC3 antibody L-chain (SEQ ID NO: 13)

```
AAGCTTGCATGCCTGCAGGTCGACTCTAGAGGATCCGTCGACATTGATTA

TTGACTAGTTATTAATAGTAATCAATTACGGGGTCATTAGTTCATAGCCC

ATATATGGAGTTCCGCGTTACATAACTTACGGTAAATGGCCCGCCTGGCT

GACCGCCCAACGACCCCCGCCCATTGACGTCAATAATGACGTATGTTCCC

ATAGTCAATAGGGACTTTCCATTGACGTCAATGGGTGGAGTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTCGAGGTGAGCCCCACGTTCTGCTTCACTCTCCCC

ATCTCCCCCCCCTCCCCACCCCCAATTTTGTATTTATTTTATTTTLTTAA

TTATTTTGTGCAGCGATGGGGGCGGGGGGGGGGGGGGGGCGCGCGCCAGG

CGGGGCGGGGCGGGGCGAGGGGCGGGGCGGGGCGAGGCGGAGAGGTGCGG

CGGCAGCCAATCAGAGCGGCGCGCTCCGAAAGTTTCCTTTTATGGCGAGG

CGGCGGCGGCGGCGGCCCTATAAAAAGCGAAGCGCGCGGCGGGCGGGAGT

CGCTGCGCGCTGCCTTCGCCCCGTGCCCCGCTCCGCCGCCGCCTCGCGCC

GCCCGCCCCGGCTCTGACTGACCGCGTTACTCCCACAGGTGAGCGGGCGG

GACGGCCCTTCTCCTGCGGGCTGTAATTAGCGCTTGGTTTAATGACGGCT

TGTTTCTTTTCTGTGGCTGCGTGAAAGCCTTGAGGGGCTCCGGGAGGGCC

CTTTGTGCGGGGGAGCGGCTCGGGGGTGCGTGCGTGTGTGTGCGTG

GGGAGCGCCGCGTGCGGCTCCGCGCTGCCCGGCGGCTGTGAGCGCTGCGG

GCGCGGCGCGGGCTTTGTGCGCTCCGCAGTGTGCGCGAGGGGAGCGCGG

CCGGGGGCGGTGCCCCGCGGTGCGGGGGGGCTGCGAGGGGAACAAAGGC

TGCGTGCGGGGTGTGTGCGTGGGGGGGTGAGCAGGGGGTGTGGGCGCGTC

GGTCGGGCTGCAACCCCCCCTGCACCCCCCTCCCCGAGTTGCTGAGCACG

GCCCGGCTTCGGGTGCGGGGCTCCGTACGGGGCGTGGCGCGGGGCTCGCC

GTGCCGGGCGGGGGGTGGCGGCAGGTGGGGGTGCCGGGCGGGGCGGGGCC

GCCTCGGGCCGGGGAGGGCTCGGGGGAGGGGCGCGGCGGCCCCCGGAGCG

CCGGCGGCTGTCGAGGCGCGGCGAGCCGCAGCCATTGCCTTTTATGGTAA

TCGTGCGAGAGGGCGCAGGGACTTCCTTTGTCCCAAATCTGTGCGGAGCC

GAAATCTGGGAGGCGCCGCCGCACCCCCTCTAGCGGGCGCGGGGCGAAGC

GGTGCGGCGCCGGCAGGAAGGAAATGGGCGGGGAGGGCCTTCGTGCGTCG

CCGCGCCGCCGTCCCCTTCTCCCTCTCCAGCCTCGGGGCTGTCCGCGGGG

GGACGGCTGCCTTCGGGGGGGACGGGGCAGGGCGGGGTTCGGCTTCTGGC

GTGTGACCGGCGGCTCTAGAGCCTCTGCTAACCATGTTCATGCCTTCTTC

TTTTTCCTACAGCTCCTGGGCAACGTGCTGGTTATTGTGCTGTCTCATCA

TTTTGGCAAAGAATTCCTCGAGCCACCATGAGGCTCCCTGCTCAGCTCCT

GGGGCTGCTAATGCTCTGGGTCTCTGGATCCAGTGGGGATGTTGTGATGA

CTCAGTCTCCACTCTCCCTGCCCGTCACCCCTGGAGAGCCGGCCTCCATC

TCCTGCAGATCTAGTCAGAGCCTTGTACACAGTAATAGGAACACCTATTT

ACATTGGTACCTGCAGAAGCCAGGGCAGTCTCCACAGCTCCTGATCTATA

AAGTTTCCAACCGATTTTCTGGGGTCCCTGACAGGTTCAGTGGCAGTGGA

TCAGGCACAGATTTTACACTGAAAATCAGCAGAGTGGAGGCTGAGGATGT

TGGGGTTTATTACTGCTCTCAAAATACACATGTTCCTCCTACGTTTGGCC

AGGGGACCAAGCTGGAGATCAAACGTACGGTGGCTGCACCATCTGTCTTC

ATCTTCCCGCCATCTGATGAGCAGTTGAAATCTGGAACTGCCTCTGTTGT

GTGCCTGCTGAATAACHCTATCCCAGAGAGGCCAAAGTACAGTGGAAGGT

GGATAACGCCCTCCAATCGGGTAACTCCCAGGAGAGTGTCACAGAGCAGG

ACAGGAAGGACAGCACCTACAGCCTCAGCAGCACCCTGACGCTGAGCAAA

GCAGACTACGAGAAACACAAAGTCTACGCCTGCGAAGTCACCCATCAGGG

CCTGAGCTCGCCCGTCACAAAGAGCTTCAACAGGGGAGAGTGTTGATAAG

TCGAGGTCGAGGAATTCACTCCTCAGGTGCAGGCTGCCTATCAGAAGGTG

GTGGGTGGTGTGGCCAATGCCCTGGCTCACAAATACCACTGAGATCTTTT

TTCCCTCTGCCAAAAATTATGGGGACATCATGAAGCCCCTTGAGCATCTG

ACTTCTGGCTAATAAAGGAAATTTATTTTCATTGCAATAGTGTGTTGGAA

TTTTTGTGTCTCTCACTCGGAAGGACATATGGGAGGGCAAATCATTTAA

AACATCAGAATGAGTATTTGGTTTAGAGTTTGGCAACATATGCCCATATG

CTGGCTGCCATGAACAAAGGTTGGCTATAAAGAGGTCATCAGTATATGAA

ACAGCCCCTGCTGTCCATTCCTTATTCCATAGAAAAGCCTTGACTTGAG

GTTAGATTTTTTTTATATTTGTTTTGTGTTATTTTTTTCTTTAACATC

CCTAAAATTI TCCTTACATGTTTTACTAGCCAGATTTTTCCTCCTCTCCT

GACTACTCCCAGTCATAGCTGTCCCTCTTCTCTTATGGAGATCCCTCGAC

CTGCAGCCCAAGCTT
```

Example 1-3

Production of V209 nGlm(1) Allotype

For obtaining an nGlm(1) allotype of V209, a Glm(1) allotype thereof, a cassette for nGhn(1) allotype was formed. Specifically, using forward primer HerSmaF and reverse primer HerNotR shown by SEQ ID NO: 14 and NO:15, and using, as a template, the anti-GPC3 antibody H-chain gene shown by SEQ ID NO:10 and produced in Example 1-2, PCR was carried out under the condition mentioned below.

×10 KOD buffer 5 µl, dNTPs and MgCl₂ 5 µl and 2 µl, respectively, (attached to KOD polymerase, Toyobo) were mixed. The primer combination as above (20 µmole/l, 1 µl each), GPC3 antibody H-chain gene 1 µl, dH₂O 34.5 µl, and 5 units/µl KOD polymerase 0.5 µl were added to make 50 µl in total. PCR was carried out under the condition mentioned below.

96° C. 1 min; (98° C. 15 sec; 65° C. 2 sec; 74° C. 30 sec)×35 cycles; 74° C. 30 sec; 4° C.

The fragment obtained was subcloned into pBluescriptSK⁺ (pBher), and its sequence was confirmed. Next, an SmaI-NotI fragment of about 290 bp was cut out from pC-aGPChl(209) described in Example 1-2. On the other hand, SmaI-NotI fragment was cut out from pBher in the same manner, and the fragment of about 290 bp was introduced into the corresponding site of pC-aGPChl(209) for substitution to obtain a nGlm (1) allotype expression vector (pC-aGPChl(209Her)).

```
Forward primer: HerSmaF
                                    (SEQ ID NO: 14)
gggaggagatgaccaagaaccaggtcaccctgacctgcc Reverse primer: HerNotR
                                    (SEQ ID NO: 15)
tttgcggccgcttatcatttacccggagacagggagaggctc
```

Example 2

Preparation of Fc-Modified Anti-GPC3 Antibody

Example 2-1

Expression of Fc-Modified Anti-GPC3 Antibody in CHO Cells

Ten microliters of Fc-modified anti-GPC3 antibody expression vector pC-aGPChl(22), pC-aGPChl(209), pC-aGPChl(212), pC-aGPChl(922), pC-aGPChl(1608) or pC-aGPChl(209Her) was cleaved with PvuI to give a linear DNA. This was introduced into 2×10⁶/0.6 ml PBS(−) of CHO cells (strain DXB11S) according to an electroporation method under a condition of 1.5 kV and 25 uF. The cells were incubated in a 8% CO₂ incubator at 37° C. The cells were screened in CHO-S-SFMII medium (Invitrogen) containing 400 µg/ml of geneticin. Selected cells were inoculated into a CHO-S-SFMII medium containing 400 µg/ml geneticin in a 96-well plate at 0.4 cells/100 µl well, and the cells were cloned according to a limiting dilution method. The culture supernatant was analyzed with BIACORE 3000. The antigen was quantified using a chip with fused protein GST-GPC3 (antigen GST and human glypican-3 shown by SEQ ID NO:16) immobilized thereon, and high-expression cells were selected.

```
Amino acid sequence of GPC3 peptide
                                    (SEQ ID NO: 16)
AELAYDLDVDDAPGNSQQATPKDNEISTFHNLGNVHSPLK
```

Example 2-2

Purification of Fc-Modified Anti-GPC3 Antibody

The culture supernatant of CHO cells expressing Fc-modified humanized glypican antibody was applied to an rProtein A Sepharose Fast Flow column equilibrated with 150 mM NaCl-containing 10 mM citrate-phosphate buffer (pH 7.5). The column was washed with the same buffer, 1 M NaCl-containing 10 mM citrate-phosphate buffer (pH 7.5), then 10 mM citrate-phosphate buffer (pH 7.5), and the protein adsorbed to the column was eluted out with 20 mM acetic acid. To the 20 mM acetic acid fraction containing Fc-modified humanized anti-glypican antibody, 1 M tris-HCl buffer (pH 8.5) was added to adjust pH of from 5 to 6, and was filtered through a 0.22 µm filter. An equivalent amount of MilliQ water was added to the thus-filtered fraction, and applied to SP Sepharose Fast Flow column equilibrated with 20 mM acetate buffer (pH 6.0). The column was washed with the same buffer, and then the protein adsorbed to the column was eluted out with 20 mM NaCl-containing 20 mM acetate buffer (pH 6.0) to obtain a purified fraction of Fc-modified humanized anti-glypican antibody.

Figure 2:
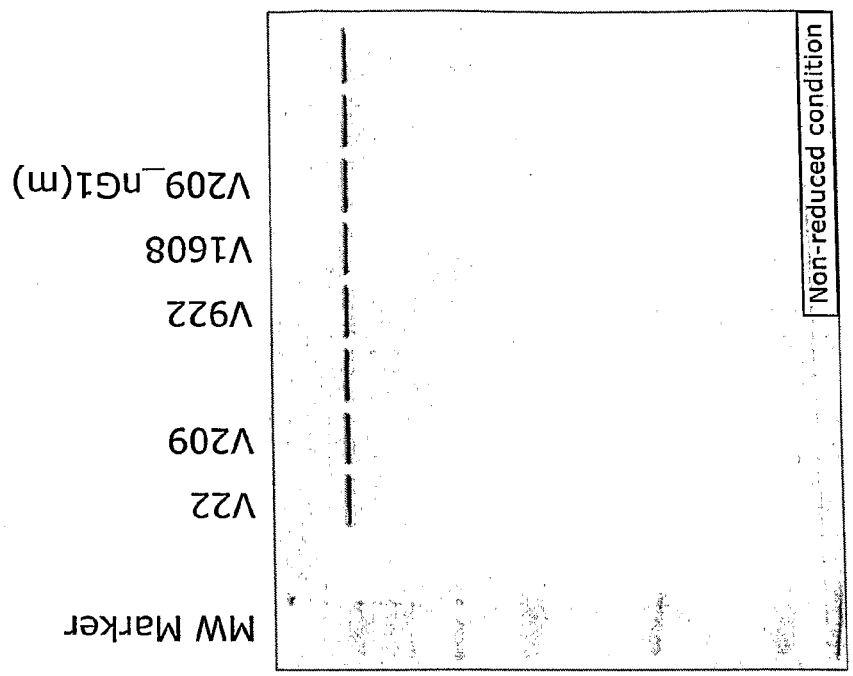
FIG. 2 shows the result of SDS-PAGE analysis of a purified Fc-modified humanized anti-glypican-3 antibody of the invention.
Figure 2:
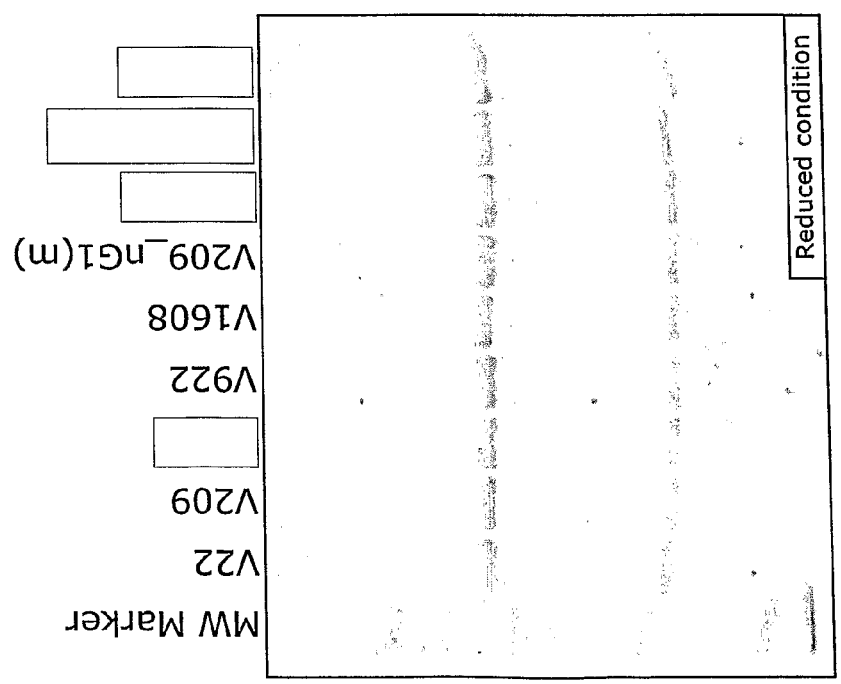

FIG. 2 shows the result of SDS-PAGE (polyacrylamide gel electrophoresis) of a purified Fc-modified humanized anti-glypican antibody of the invention in a known method (Nature, 227, 680, 1970, hereby incorporated by reference in its entirety) to analyze the molecular weight and the degree of purification of the antibody. Each purified Fc-modified humanized anti-glypican antibody provided a single band at a molecular weight of about 150 kDa under a non-reducing condition and provided two bands at about 50 kDa and about 25 kDa under a reducing condition. These molecular weights substantially agree with those presumed from the nucleotide sequence of the H-chain and L-chain cDNAs of the antibody, and further agree with the report that an IgG-type antibody has a molecular weight of about 150 kDa under a non-reducing condition, and an H-chain having a molecular weight of about 50 kDa and an L-chain having a molecular weight of about 25 kDa under a reducing condition, where its intramolecular disulfide bond is cleaved (Antibodies, Chapter 14, Monoclonal Antibodies, hereby incorporated by reference in its entirety). It has been confirmed that each Fc-modified humanized anti-glypican antibody was expressed as an antibody molecule having a correct structure and was purified as such.

Figure 3:
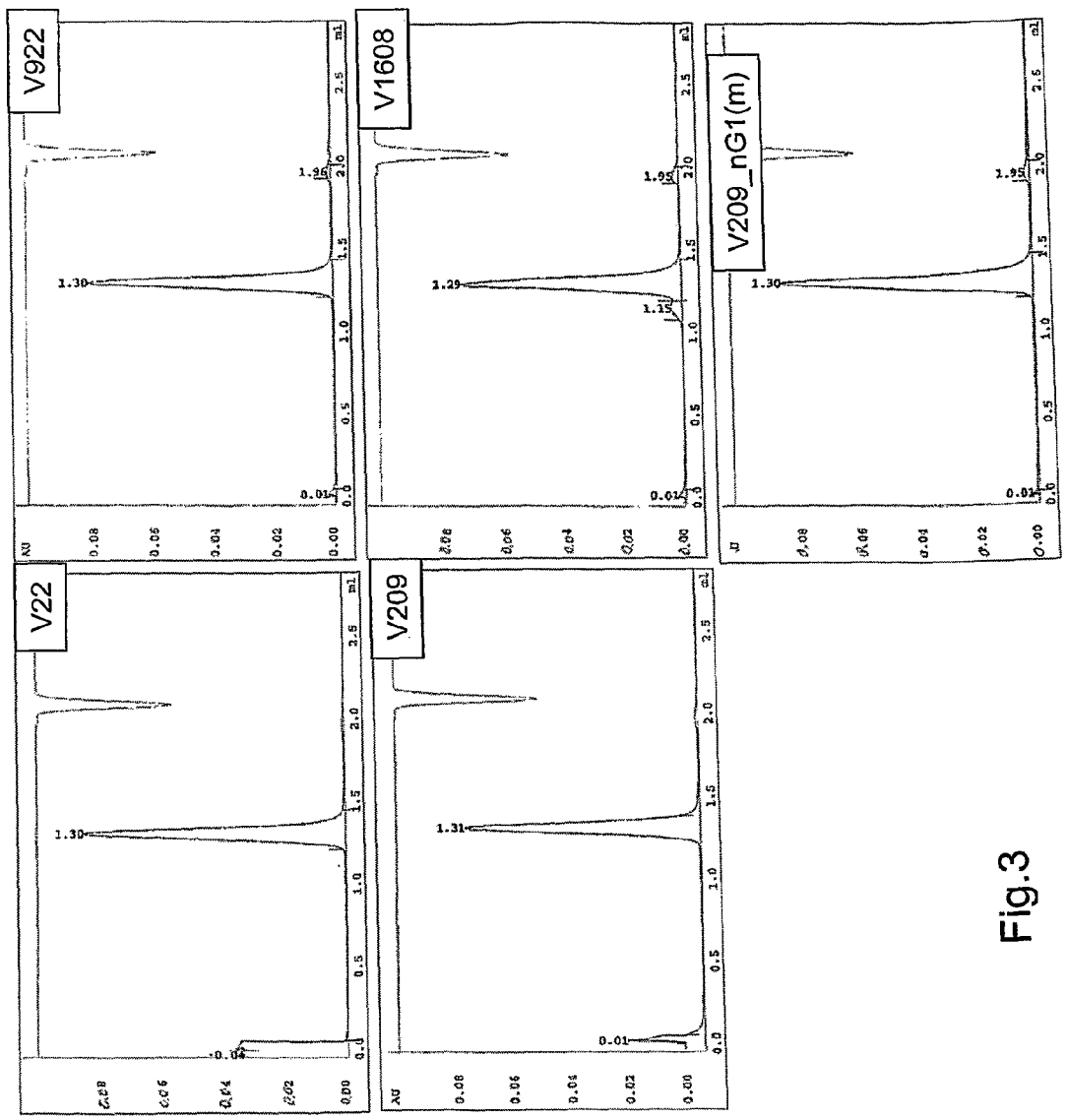
FIG. 3 shows a chromatogram of a purified Fc-modified humanized anti-glypican-3 antibody analyzed through a gel permeation column.

FIG. 3 shows a chromatogram of a purified Fc-modified humanized anti-glypican-3 antibody analyzed through a gel permeation column (Superdex 200 PC3.2/30, by GE Amersham Biosciences).

Example 3

Measurement of ADCC Activity of Fc-Modified Anti-GPC3 Antibody

Example 3-1 cDNA Cloning of Human Glypican-3 (GPC3)

A full-length cDNA coding for human GPC3 was amplified through PCR using Advantage2 kit (CLONETECH) and, as a template, 1st strand cDNA having been prepared from colon cancer cell line Caco2 in an ordinary manner. Specifically, 50 µl of a reaction solution containing 2 µl of Caco2-derived cDNA, 1 µl of sense primer (GATATC-ATGGCCGG-GACCGTGCGCACCGCGT, SEQ ID NO: 17), 1 µl of antisense primer (GCTAGC-TCAGTGCACCAGGAAGAA-GAAGCAC, SEQ ID NO: 18), 5 µl of Advantage2 10×PCR buffer, 8 µl of dNTX mix (1.25 mM) and 1.0 µl of Advantage polymerase Mix, was subjected to 35 cycles of 94° C. 1 min; 63° C. 30 sec; 68° C. 3 min. The PCR amplified product was inserted into a TA vector pGEM-Teasy by the use of pGEM-T Easy Vector System I (Promega). The sequence of the product was confirmed using ABI3100 DNA sequencer. In this way, cDNA coding for the full length of human GPC3 was isolated. The nucleotide sequence of human GPC3 gene is shown in SEQ ID NO:19, and the amino acid sequence of human GPC3 protein is shown in SEQ ID NO:20.

Example 3-2

Preparation of Human Hepatic Cancer Cell Line (SK-03) Expressing Full-Length GPC3

To obtain a cell line for evaluating the biological activity of anti-GPC3 antibody, a human hepatic cell line capable of expressing a full-length GPC3 was established.

One μg of full-length human GPC3 gene expression vector treated with PvuI was mixed with 2 μl of FuGENE (Roche) to form a complex, and then this was added to SK-HEP-1 cells (purchased from ATCC) for gene introduction. The cells were incubated in a $CO_2$ incubator for 24 hours, and then, GPC3-expressing cells were selected using Dulbecco MEM (D-MEM, by SIGMA) containing geneticin (Invitrogen) at a final concentration of 1 mg/ml and 10% FBS. The thus-obtained geneticin-resistant colonies were collected, and the cells were cloned according to a limiting dilution method. The expression of human GPC3 in each cell clone was determined by flow cytometry using chimera GC33 antibody and FITC-labeled goat anti-human IgG antibody (ICN) to obtain a stable expression cell line SK-03 was obtained.

Example 3-3

Measurement of ADCC Activity with Human Peripheral Blood-Derived PBMC

Example 3-3-1

Preparation of Human PBMC Solution

Heparin-added peripheral blood was collected from a healthy person, diluted 2-fold with PBS(−) and overlaid on Ficoll-Paque™ PLUS (Amersham). After centrifugation (500×g, 30 minutes, 20° C.), the interlayer of a monocyte fraction was collected. The monocytes were washed three times and suspended in 10% FBS/RPMI to prepare a human PBMC solution.

Example 3-3-2

Preparation of Target Cells

SK-03 cells were maintained in D-MEM medium (SIGMA) containing 1 mg/ml of geneticin and 10% FBS (ThermoTrace). The cells were peeled from the dish using Cell Dissociation Buffer (Invitrogen), and transferred to each well of a 96-well U-bottomed plate (Falcon) at $1\times10$ cells/well, and incubated for 1 day. After the incubation, 5.55 MBq of Chromium-51 was added and the cells were further incubated in a 5% $CO_2$ incubator at 37° C. for 4 hours. The cells were washed once with the medium, and suspended in 50 μl of 10% FBS/RPMI1640 medium to prepare target cells.

Example 3-3-3

Chromium Release Test (ADCC Activity)

Fifty μl of an antibody solution prepared to have a predetermined concentration was added to the target cells, and reacted at room temperature for 15 minutes. Next, 100 μl of the human PBMC solution was added ($5\times10^5$ cells/well), and centrifuged, and then incubated in a 5% $CO_2$ incubator at 37° C. for 4 hours. After the incubation, the plate was centrifuged, and the radioactivity of 100 μl of the culture supernatant was counted with a gamma counter. The specific chromium release ratio of the sample was obtained according to the following formula:

$$\text{Specific Chromium Release Ratio}(\%)=(A-C)\times100/(B-C)$$

wherein A indicates a mean value of the radioactivity (cpm) in each well; B indicates a mean value of the radioactivity (cpm) of each well, in which 100 μl of aqueous 2% NP-40 solution (Nonidet P-40, Code No. 252-23, by Nacalai Tesque) and 50 μl of 10% FBS/RPMI medium were added to the target cells; C indicates a mean value of the radioactivity (cpm) of each well, in which 150 μl of 10% FBS/RPMI medium was added to the target cells.

The experiment was carried out in triplicate, and the mean value of the ADCC activity (%) of the sample was calculated.

Figure 4:
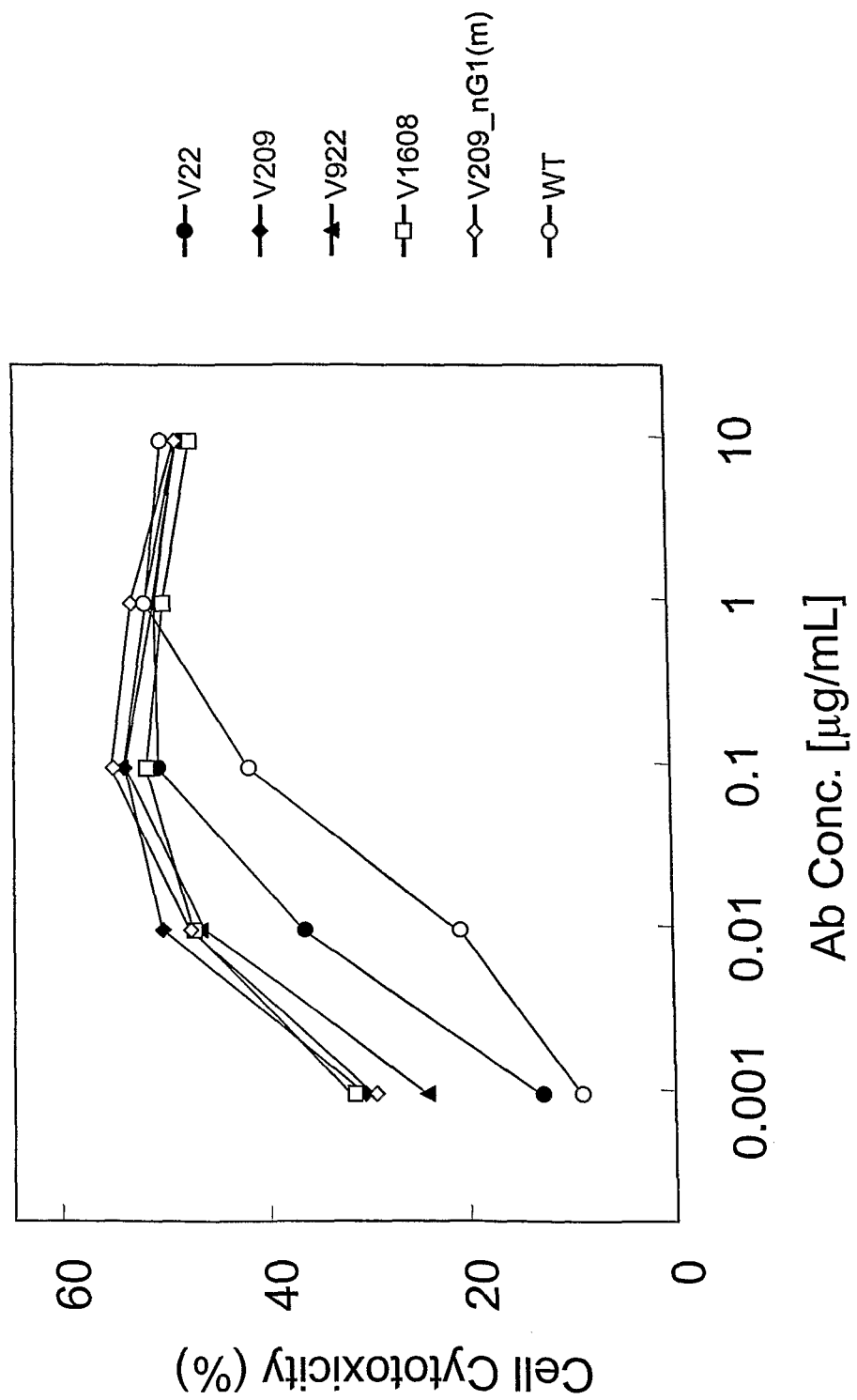
FIG. 4 shows the ADCC activity against SK-03 cells of the Fc-modified and wild-type humanized anti-glypican-3 antibodies, using human peripheral blood-derived PBMC.

The results are shown in FIG. 4. The Fc-modified humanized anti-glypican antibodies V22, V209, V922, V1608 and V209(nGlm(1)) all had enhanced ADCC activity compared to the wild-type antibody (WT). Of those, the activity of V22 was lower than that of the others, but there was found little difference in the activity between V209, V922, V1608 and V209(nGlm(1)).

Example 3-4

Measurement of ADCC Activity Using Mouse Marrow-Derived Effector Cells

Example 3-4-1

Preparation of Mouse Marrow-Derived Effector Cell Suspension

Marrow cells were collected from the thigh bone of an SCID mouse (from Nippon Clea, male, 10 weeks old), and suspended in 10% FBS/RPMI1640 medium at a density of $5\times10^5$ cells/ml. Mouse GM-CSF (Pepro Tech) and human IL-2 (Pepro Tech) were added at a final concentration of 10 ng/ml and 50 ng/ml, respectively. The cells were incubated in a 5% $CO_2$ incubator at 37° C. for 5 days. After the incubation, the cells were peeled with a scraper, washed once with the medium, and suspended in 10% FBS/RPMI1640 medium at a density of $5\times10$ cells/ml to prepare a mouse marrow-derived effector cell suspension.

Example 3-4-2

Preparation of Target Cells

Human hepatic cancer cells HepG2 (purchased from ATCC) were maintained in RPMI1640 medium (SIGMA) containing 10% FBS (Thermo Trace). The cells were peeled from the dish using Cell Dissociation Buffer (Invitrogen), and transferred to each well of a 96-well U-bottomed plate (Falcon) at a density of $1\times10^4$ cells/well, and incubated for 1 day. After the incubation, 5.55 MBq of Chromium-51 was added and the cells were further incubated in a 5% $CO_2$ incubator at 37° C. for 4 hours. The cells were washed once with the medium, and suspended in 50 μl of 10% FBS/RPMI1640 medium to prepare target cells.

Example 3-4-3

Chromium Release Test (ADCC Activity)

Fifty μl of an antibody solution prepared to have a predetermined concentration was added to the target cells, and reacted at room temperature for 15 minutes. Next, 100 μl of the mouse marrow-derived effector cell suspension was added (5×10⁵ cells/well), and centrifuged, and then incubated in a 5% $CO_2$ incubator at 37° C. for 4 hours. After the incubation, the plate was centrifuged, and the radioactivity of 100 μl of the culture supernatant was counted with a gamma counter. The specific chromium release ratio of the sample was obtained according to the following formula:

Specific Chromium Release Ratio(%)=$(A-C) \times 100 / (B-C)$ wherein A indicates a mean value of the radioactivity (cpm) in each well; B indicates a mean value of the radioactivity (cpm) of each well, in which 100 μl of aqueous 2% NP-40 solution (Nonidet P-40, Code No. 252-23, by Nacalai Tesque) and 50 μl of 10% FBS/RPMI medium were added to the target cells; C indicates a mean value of the radioactivity (cpm) of each well, in which 150 μl of 10% FBS/RPMI medium was added to the target cells.

The experiment was carried out in triplicate, and the mean value of the ADCC activity (%) of the sample was calculated.

Figure 5:
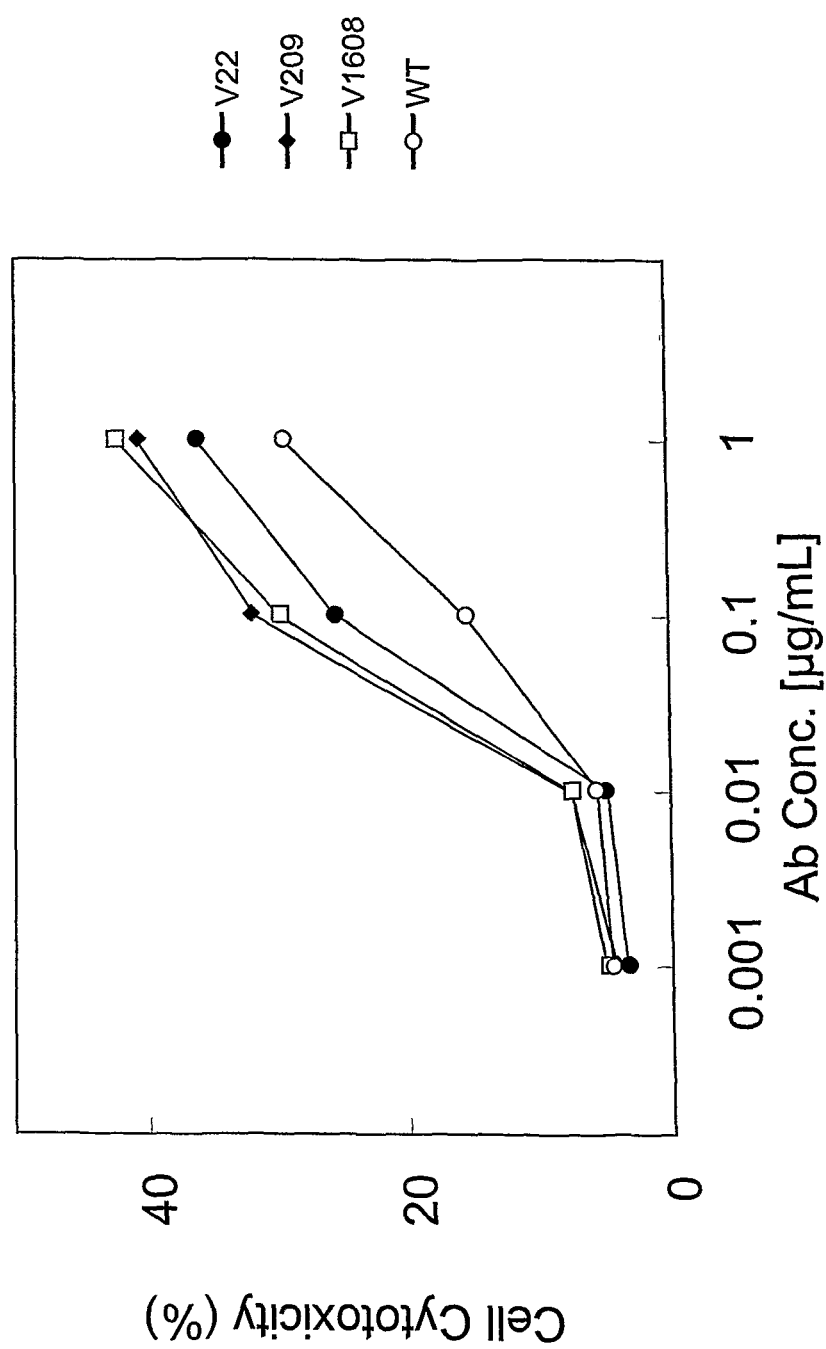
FIG. 5 shows the ADCC activity against HepG2 cells of the Fc-modified and wild-type humanized anti-glypican-3 antibodies, using mouse marrow-derived effector cells.

The results are shown in FIG. 5. The Fc-modified humanized anti-glypican antibodies V22, V209 and V1608 all had enhanced ADCC activity compared to the wild-type antibody (WT).

INDUSTRIAL UTILITY

The Fc-modified humanized anti-glypican-3 antibody is useful in treating cancers, such as hepatic cancer.

What is claimed is:

1. An anti-glypican-3 antibody comprising an Fc region having aspartic acid at EU numbering position 239, threonine at EU numbering position 326, alanine at EU numbering position 330, and glutamic acid at EU numbering position 332 of the Fc region,
wherein the anti-glypican-3 antibody comprises a H-chain CDR1 as set forth in SEQ ID NO:23, a H-chain CDR2 as set forth in SEQ ID NO:24, and a H-chain CDR3 as set forth in SEQ ID NO:25, and comprises a L-chain CDR1 as set forth in SEQ ID NO:26, a L-chain CDR2 as set forth in SEQ ID NO:27, and a L-chain CDR3 as set forth in SEQ ID NO:28.

2. An anti-glypican-3 antibody comprising an Fc region having aspartic acid at EU numbering position 239, alanine at EU numbering position 298, glutamic acid at EU numbering position 326, alanine at EU numbering position 330, and glutamic acid at EU numbering position 332 of the Fc region,
wherein the anti-glypican-3 antibody comprises a H-chain CDR1 as set forth in SEQ ID NO:23, a H-chain CDR2 as set forth in SEQ ID NO:24, and a H-chain CDR3 as set forth in SEQ ID NO:25, and comprises a L-chain CDR1 as set forth in SEQ ID NO:26, a L-chain CDR2 as set forth in SEQ ID NO:27, and a L-chain CDR3 as set forth in SEQ ID NO:28.

3. A method for producing an anti-glypican-3 antibody, the method comprising:
(i) culturing a host cell engineered to express nucleic acid encoding the anti-glypican-3 antibody of claim 1; and
(ii) isolating said antibody from the culture.

4. A method for producing an anti-glypican-3 antibody, the method comprising:
(i) culturing a host cell engineered to express nucleic acid encoding the anti-glypican-3 antibody of claim 2; and
(ii) isolating said antibody from the culture.

5. An anti-glypican-3 antibody having a CH2-CH3 domain comprising the amino acid sequence set forth in SEQ ID NO: 37, wherein the anti-glypican-3 antibody comprises a H-chain CDR1 as set forth in SEQ ID NO:23, a H-chain CDR2 as set forth in SEQ ID NO:24, and a H-chain CDR3 as set forth in SEQ ID NO:25, and comprises a L-chain CDR1 as set forth in SEQ ID NO:26, a L-chain CDR2 as set forth in SEQ ID NO:27, and a L-chain CDR3 as set forth in SEQ ID NO:28.

6. A pharmaceutical composition comprising the anti-glypican-3 antibody as claimed in claim 5 and a pharmaceutically acceptable carrier.

7. A method of treating a patient with hepatic cancer comprising administering to the patient the pharmaceutical composition as claimed in claim 6.

8. An anti-glypican-3 antibody having a CH2-CH3 domain comprising the amino acid sequence set forth in SEQ ID NO: 38, wherein the anti-glypican-3 antibody comprises a H-chain CDR1 as set forth in SEQ ID NO:23, a H-chain CDR2 as set forth in SEQ ID NO:24, and a H-chain CDR3 as set forth in SEQ ID NO:25, and comprises a L-chain CDR1 as set forth in SEQ ID NO:26, a L-chain CDR2 as set forth in SEQ ID NO:27, and a L-chain CDR3 as set forth in SEQ ID NO:28.

9. A pharmaceutical composition comprising the anti-glypican-3 antibody as claimed in claim 8 and a pharmaceutically acceptable carrier.

10. A method of treating a patient with hepatic cancer comprising administering to the patient the pharmaceutical composition as claimed in claim 9.

11. A pharmaceutical composition comprising the anti-glypican-3 antibody as claimed in claim 1 and a pharmaceutically acceptable carrier.

12. A method of treating a patient with hepatic cancer comprising administering to the patient the pharmaceutical composition as claimed in claim 11.

13. A pharmaceutical composition comprising the anti-glypican-3 antibody as claimed in claim 2 and a pharmaceutically acceptable carrier.

14. A method of treating a patient with hepatic cancer comprising administering to the patient the pharmaceutical composition as claimed in claim 13.

15. The anti-glypican-3 antibody of claim 1, wherein the Fc region is an Fc region of an IgG1 antibody.

16. The anti-glypican-3 antibody of claim 15, wherein the amino acid sequence of the Fc region, with the exception of aspartic acid at EU numbering position 239, threonine at EU numbering position 326, and glutamic acid at EU numbering position 332, is the amino acid sequence of the Fc region of wild-type human IgG1 antibody.

17. The anti-glypican-3 antibody of claim 2, wherein the Fc region is an Fc region of an IgG1 antibody.

18. The anti-glypican-3 antibody of claim 17, wherein the amino acid sequence of the Fc region, with the exception of aspartic acid at EU numbering position 239, alanine at EU numbering position 298, glutamic acid at EU numbering position 326, and glutamic acid at EU numbering position 332, is the amino acid sequence of the Fc region of wild-type human IgG1 antibody.

19. The anti-glypican-3 antibody of claim 5, wherein the antibody comprises a heavy chain variable domain as set forth in SEQ ID NO: 21 and a light chain variable domain as set forth in SEQ ID NO: 22.

20. The anti-glypican-3 antibody of claim 19, wherein the antibody comprises a heavy chain as set forth in SEQ ID NO: 32 and a light chain encoded by SEQ ID NO: 13.

21. A method for producing an anti-glypican-3 antibody, the method comprising:
   (i) culturing a host cell engineered to express nucleic acid encoding the anti-glypican-3 antibody of claim 5; and
   (ii) isolating said antibody from the culture.

22. The anti-glypican-3 antibody of claim 8, wherein the antibody comprises a heavy chain variable domain as set forth in SEQ ID NO: 21 and a light chain variable domain as set forth in SEQ ID NO: 22.

23. The anti-glypican-3 antibody of claim 22, wherein the antibody comprises a heavy chain as set forth in SEQ ID NO: 33 and a light chain encoded by SEQ ID NO: 13.

24. A method for producing an anti-glypican-3 antibody, the method comprising:
   (i) culturing a host cell engineered to express nucleic acid encoding the anti-glypican-3 antibody of claim 8; and
   (ii) isolating said antibody from the culture.

* * * * *

SEQUENCE LISTING

```
<160> NUMBER OF SEQ ID NOS: 38

<210> SEQ ID NO 1
<211> LENGTH: 96
<212> TYPE: DNA
<213> ORGANISM: Artificial Sequence
<220> FEATURE:
<223> OTHER INFORMATION: PCR primer

<400> SEQUENCE: 1
agttcaactg gtacgtggac ggcgtggagg tgcataatgc caagacaaag ccgcgggagg      60
agcagtacaa cgccacgtac cgtgtggtca gcgtcc                               96

<210> SEQ ID NO 2
<211> LENGTH: 93
<212> TYPE: DNA
<213> ORGANISM: Artificial Sequence
<220> FEATURE:
<223> OTHER INFORMATION: PCR primer

<400> SEQUENCE: 2
tctcccggac ccctgaggtc acatgcgtgg tggtggacgt gagccacgaa gaccctgagg      60
tcaagttcaa ctggtacgtg gacggcgtgg agg                                   93

<210> SEQ ID NO 3
<211> LENGTH: 97
<212> TYPE: DNA
<213> ORGANISM: Artificial Sequence
<220> FEATURE:
<223> OTHER INFORMATION: PCR primer

<400> SEQUENCE: 3
gcacctgagc tcctgggggg accggacgtc ttcctcttcc ccccaaaacc caaggacacc      60
ctcatgatct cccggacccc tgaggtcaca tgcgtgg                               97

<210> SEQ ID NO 4
<211> LENGTH: 94
<212> TYPE: DNA
<213> ORGANISM: Artificial Sequence
<220> FEATURE:
<223> OTHER INFORMATION: PCR primer

<400> SEQUENCE: 4
```
ggagaccttg cacttgtact ccttgccatt cagccagtcc tggtgcagga cggtgaggac    60
gctgaccaca cggtacgtgg cgttgtactg ctcc                                94

<210> SEQ ID NO 5
<211> LENGTH: 91
<212> TYPE: DNA
<213> ORGANISM: Artificial Sequence
<220> FEATURE:
<223> OTHER INFORMATION: PCR primer

<400> SEQUENCE: 5
ggctgccctt tggctttgga gatggttttc tcctcgggca gtgggagggc tttgttggag    60
accttgcact tgtactcctt gccattcagc c                                   91

<210> SEQ ID NO 6
<211> LENGTH: 91
<212> TYPE: DNA
<213> ORGANISM: Artificial Sequence
<220> FEATURE:
<223> OTHER INFORMATION: PCR primer

<400> SEQUENCE: 6
ggctgccctt tggctttgga gatggttttc tcctcggggg ctgggagggc tttgttggag    60
accttgcact tgtactcctt gccattcagc c                                   91

<210> SEQ ID NO 7
<211> LENGTH: 91
<212> TYPE: DNA
<213> ORGANISM: Artificial Sequence
<220> FEATURE:
<223> OTHER INFORMATION: PCR primer

<400> SEQUENCE: 7
ggctgccctt tggctttgga gatggttttc tcctcggggg ctgggagggc ggtgttggag    60
accttgcact tgtactcctt gccattcagc c                                   91

<210> SEQ ID NO 8
<211> LENGTH: 91
<212> TYPE: DNA
<213> ORGANISM: Artificial Sequence
<220> FEATURE:
<223> OTHER INFORMATION: PCR primer

<400> SEQUENCE: 8
ggctgccctt tggctttgga gatggttttc tcctcggggg ctgggagggc ctcgttggag    60
accttgcact tgtactcctt gccattcagc c                                   91

<210> SEQ ID NO 9
<211> LENGTH: 81
<212> TYPE: DNA
<213> ORGANISM: Artificial Sequence
<220> FEATURE:
<223> OTHER INFORMATION: PCR primer

<400> SEQUENCE: 9
gagctccccg ggatgggggc agggtgtaca cctgtggttc tcggggctgc cctttggctt    60
tggagatggt tttctcctcg g                                              81

<210> SEQ ID NO 10
<211> LENGTH: 1422
<212> TYPE: DNA
<213> ORGANISM: Artificial Sequence
<220> FEATURE:
<223> OTHER INFORMATION: humanized antibody H-chain

<400> SEQUENCE: 10

| | | | | | |
|---|---|---|---|---|---|
| gaattccacc | atggactgga | cctggaggtt | cctctttgtg | gtggcagcag | ctacaggtgt | 60 |
| ccagtcccag | gtgcagctgg | tgcagtctgg | agctgaggtg | aagaagcctg | ggcctcagt | 120 |
| gaaggtctcc | tgcaaggctt | ctggatacac | cttcaccgac | tatgaaatgc | actgggtgcg | 180 |
| acaggcccct | ggacaagggc | ttgagtggat | gggagctctt | gatcctaaaa | ctggtgatac | 240 |
| tgcctacagt | cagaagttca | agggcagagt | cacgctgacc | gcggacaaat | ccacgagcac | 300 |
| agcctacatg | gagctgagca | gcctgacatc | tgaggacacg | gccgtgtatt | actgtacaag | 360 |
| attctactcc | tatacttact | ggggccaggg | aaccctggtc | accgtctcct | cagctagcac | 420 |
| caagggccca | tcggtcttcc | ccctggcacc | ctcctccaag | agcacctctg | ggggcacagc | 480 |
| ggccctgggc | tgcctggtca | aggactactt | ccccgaaccg | gtgacggtgt | cgtggaactc | 540 |
| aggcgccctg | accagcggcg | tgcacacctt | cccggctgtc | ctacagtcct | caggactcta | 600 |
| ctccctcagc | agcgtggtga | ccgtgccctc | cagcagcttg | ggcacccaga | cctacatctg | 660 |
| caacgtgaat | cacaagccca | gcaacaccaa | ggtggacaag | aaagttgagc | ccaaatcttg | 720 |
| tgacaaaact | cacacatgcc | caccgtgccc | agcacctgaa | ctcctggggg | gaccgtcagt | 780 |
| cttcctcttc | cccccaaaac | ccaaggacac | cctcatgatc | tcccggaccc | ctgaggtcac | 840 |
| atgcgtggtg | gtggacgtga | gccacgaaga | ccctgaggtc | aagttcaact | ggtacgtgga | 900 |
| cggcgtggag | gtgcataatg | ccaagacaaa | gccgcgggag | gagcagtaca | acagcacgta | 960 |
| ccgtgtggtc | agcgtcctca | ccgtcctgca | ccaggactgg | ctgaatggca | aggagtacaa | 1020 |
| gtgcaaggtc | tccaacaaag | ccctcccagc | ccccatcgag | aaaaccatct | ccaaagccaa | 1080 |
| agggcagccc | cgagaaccac | aggtgtacac | cctgccccca | tcccgggatg | agctgaccaa | 1140 |
| gaaccaggtc | agcctgacct | gcctggtcaa | aggcttctat | cccagcgaca | tcgccgtgga | 1200 |
| gtgggagagc | aatgggcagc | cggagaacaa | ctacaagacc | acgcctcccg | tgctggactc | 1260 |
| cgacggctcc | ttcttcctct | acagcaagct | caccgtggac | aagagcaggt | ggcagcaggg | 1320 |
| gaacgtcttc | tcatgctccg | tgatgcatga | ggctctgcac | aaccactaca | cgcagaagag | 1380 |
| cctctccctg | tctccgggta | aatgataagc | ggccgcggat | cc | | 1422 |

<210> SEQ ID NO 11
<211> LENGTH: 45
<212> TYPE: DNA
<213> ORGANISM: Artificial Sequence
<220> FEATURE:
<223> OTHER INFORMATION: PCR primer

<400> SEQUENCE: 11
gctagcacca agggcccatc ggtcttcccc ctggcaccct cctcc       45

<210> SEQ ID NO 12
<211> LENGTH: 44
<212> TYPE: DNA
<213> ORGANISM: Artificial Sequence
<220> FEATURE:
<223> OTHER INFORMATION: PCR primer

<400> SEQUENCE: 12
gagctcaggt gctgggcacg gtgggcatgt gtgagttttg tcac       44

<210> SEQ ID NO 13

<211> LENGTH: 3067
<212> TYPE: DNA
<213> ORGANISM: Artificial Sequence
<220> FEATURE:
<223> OTHER INFORMATION: Humanized antibody L-chain

<400> SEQUENCE: 13

| | | | | | |
|---|---|---|---|---|---|
| aagcttgcat | gcctgcaggt | cgactctaga | ggatccgtcg | acattgatta | ttgactagtt | 60 |
| attaatagta | atcaattacg | gggtcattag | ttcatagccc | atatatggag | ttccgcgtta | 120 |
| cataacttac | ggtaaatggc | ccgcctggct | gaccgcccaa | cgacccccgc | ccattgacgt | 180 |
| caataatgac | gtatgttccc | atagtaacgc | caatagggac | tttccattga | cgtcaatggg | 240 |
| tggagtattt | acggtaaact | gcccacttgg | cagtacatca | agtgtatcat | atgccaagta | 300 |
| cgccccctat | tgacgtcaat | gacggtaaat | ggcccgcctg | gcattatgcc | cagtacatga | 360 |
| ccttatggga | ctttcctact | tggcagtaca | tctacgtatt | agtcatcgct | attaccatgg | 420 |
| tcgaggtgag | ccccacgttc | tgcttcactc | tccccatctc | ccccccctcc | ccacccccaa | 480 |
| ttttgtattt | atttattttt | taattatttt | gtgcagcgat | gggggcgggg | ggggggggg | 540 |
| ggcgcgcgcc | aggcggggcg | gggcggggcg | aggggcgggg | cggggcgagg | cggagaggtg | 600 |
| cggcggcagc | caatcagagc | ggcgcgctcc | gaaagtttcc | ttttatgcg | aggcggcggc | 660 |
| ggcggcggcc | ctataaaaag | cgaagcgcgc | ggcgggcggg | agtcgctgcg | cgctgccttc | 720 |
| gccccgtgcc | ccgctccgcc | gccgcctcgc | gccgcccgcc | ccggctctga | ctgaccgcgt | 780 |
| tactcccaca | ggtgagcggg | cgggacggcc | cttctcctcc | gggctgtaat | tagcgcttgg | 840 |
| tttaatgacg | gcttgtttct | tttctgtggc | tgcgtgaaag | ccttgagggg | ctccgggagg | 900 |
| gccctttgtg | cgggggagc | ggctcggggg | tgcgtgcgt | gtgtgtgtgc | gtggggagcg | 960 |
| ccgcgtgcgg | ctccgcgctg | cccggcggct | gtgagcgctg | cgggcgcggc | gcggggcttt | 1020 |
| gtgcgctccg | cagtgtgcgc | gaggggagcg | cggccggggg | cggtgccccg | cggtgcgggg | 1080 |
| ggggctgcga | ggggaacaaa | ggctgcgtgc | ggggtgtgtg | cgtgggggg | tgagcagggg | 1140 |
| gtgtgggcgc | gtcggtcggg | ctgcaacccc | ccctgcaccc | ccctccccga | gttgctgagc | 1200 |
| acggcccggc | ttcgggtgcg | gggctccgta | cggggcgtgg | cgcggggctc | gccgtgccgg | 1260 |
| gcgggggtg | gcggcaggtg | gggtgccgg | gcgggcggg | gccgcctcgg | gccggggagg | 1320 |
| gctcgggga | ggggcgcggc | ggcccccgga | gcgccgcgg | ctgtcgaggc | gcggcgagcc | 1380 |
| gcagccattg | cctttatgg | taatcgtgcg | agagggcgca | gggacttcct | ttgtcccaaa | 1440 |
| tctgtgcgga | gccgaaatct | gggaggcgcc | gccgcacccc | ctctagcggg | cgcggggcga | 1500 |
| agcggtgcgg | cgccggcagg | aaggaaatgg | gcgggaggg | ccttcgtgcg | tcgccgcgcc | 1560 |
| gccgtcccct | tctccctctc | cagcctcggg | gctgtccgcg | ggggacggc | tgccttcggg | 1620 |
| ggggacgggg | cagggcgggg | ttcggcttct | ggcgtgtgac | cggcggctct | agagcctctg | 1680 |
| ctaaccatgt | tcatgccttc | ttctttttcc | tacagctcct | gggcaacgtg | ctggttattg | 1740 |
| tgctgtctca | tcattttggc | aaagaattcc | tcgagccacc | atgaggctcc | ctgctcagct | 1800 |
| cctggggctg | ctaatgctct | gggtctctgg | atccagtggg | gatgttgtga | tgactcagtc | 1860 |
| tccactctcc | ctgcccgtca | cccctggaga | gccggcctcc | atctcctgca | gatctagtca | 1920 |
| gagccttgta | cacagtaata | ggaacaccta | tttacattgg | tacctgcaga | agccagggca | 1980 |
| gtctccacag | ctcctgatct | ataaagtttc | caaccgattt | tctggggtcc | ctgacaggtt | 2040 |
| cagtggcagt | ggatcaggca | cagatttac | actgaaaatc | agcagagtgg | aggctgagga | 2100 |
| tgttggggtt | tattactgct | ctcaaaatac | acatgttcct | cctacgtttg | gccaggggac | 2160 |

```
caagctggag atcaaacgta cggtggctgc accatctgtc ttcatcttcc cgccatctga    2220
tgagcagttg aaatctggaa ctgcctctgt tgtgtgcctg ctgaataact tctatcccag    2280
agaggccaaa gtacagtgga aggtggataa cgccctccaa tcgggtaact cccaggagag    2340
tgtcacagag caggacagca aggacagcac ctacagcctc agcagcaccc tgacgctgag    2400
caaagcagac tacgagaaac acaaagtcta cgcctgcgaa gtcacccatc agggcctgag    2460
ctcgcccgtc acaaagagct tcaacagggg agagtgttga taagtcgagg tcgaggaatt    2520
cactcctcag gtgcaggctg cctatcagaa ggtggtggct ggtgtggcca atgccctggc    2580
tcacaaatac cactgagatc ttttccctc tgccaaaaat tatggggaca tcatgaagcc    2640
ccttgagcat ctgacttctg gctaataaag gaaatttatt ttcattgcaa tagtgtgttg    2700 gaatttttg tgtctctcac tcggaaggac atatgggagg gcaaatcatt taaaacatca    2760
gaatgagtat ttggtttaga gtttggcaac atatgcccat atgctggctg ccatgaacaa    2820
aggttggcta taagaggtc atcagtatat gaaacagccc cctgctgtcc attccttatt    2880
ccatagaaaa gccttgactt gaggttagat ttttttata ttttgttttg tgttattttt    2940
ttctttaaca tccctaaaat tttccttaca tgttttacta gccagatttt tcctcctctc    3000
ctgactactc ccagtcatag ctgtccctct tctcttatgg agatccctcg acctgcagcc    3060
caagctt                                                              3067

<210> SEQ ID NO 14
<211> LENGTH: 39
<212> TYPE: DNA
<213> ORGANISM: Artificial Sequence
<220> FEATURE:
<223> OTHER INFORMATION: PCR primer

<400> SEQUENCE: 14
gggaggagat gaccaagaac caggtcaccc tgacctgcc                            39

<210> SEQ ID NO 15
<211> LENGTH: 42
<212> TYPE: DNA
<213> ORGANISM: Artificial Sequence
<220> FEATURE:
<223> OTHER INFORMATION: PCR primer

<400> SEQUENCE: 15
tttgcggccg cttatcattt acccggagac agggagaggc tc                        42

<210> SEQ ID NO 16
<211> LENGTH: 40
<212> TYPE: PRT
<213> ORGANISM: Homo sapiens

<400> SEQUENCE: 16

Ala Glu Leu Ala Tyr Asp Leu Asp Val Asp Asp Ala Pro Gly Asn Ser
1               5                   10                  15

Gln Gln Ala Thr Pro Lys Asp Asn Glu Ile Ser Thr Phe His Asn Leu
            20                  25                  30

Gly Asn Val His Ser Pro Leu Lys
        35                  40

<210> SEQ ID NO 17
<211> LENGTH: 31
<212> TYPE: DNA
<213> ORGANISM: Artificial Sequence
```

```
<220> FEATURE:
<223> OTHER INFORMATION: PCR primer

<400> SEQUENCE: 17
gatatcatgg ccgggaccgt gcgcaccgcg t                              31

<210> SEQ ID NO 18
<211> LENGTH: 31
<212> TYPE: DNA
<213> ORGANISM: Artificial Sequence
<220> FEATURE:
<223> OTHER INFORMATION: PCR primer

<400> SEQUENCE: 18
gctagctcag tgcaccagga agaagaagca c                              31

<210> SEQ ID NO 19
<211> LENGTH: 1743
<212> TYPE: DNA
<213> ORGANISM: Homo sapiens

<400> SEQUENCE: 19
atggccggga ccgtgcgcac cgcgtgcttg gtggtggcga tgctgctcag cttggacttc     60
ccgggacagg cgcagccccc gccgccgccg ccggacgcca cctgtcacca agtccgctcc    120
ttcttccaga gactgcagcc cggactcaag tgggtgccag aaactcccgt gccaggatca    180
gatttgcaag tatgtctccc taagggccca acatgctgct caagaaagat ggaagaaaaa    240
taccaactaa cagcacgatt gaacatggaa cagctgcttc agtctgcaag tatggagctc    300
aagttcttaa ttattcagaa tgctgcggtt ttccaagagg cctttgaaat tgttgttcgc    360
catgccaaga actacaccaa tgccatgttc aagaacaact acccaagcct gactccacaa    420
gcttttgagt ttgtgggtga attttcaca gatgtgtctc tctacatctt gggttctgac    480
atcaatgtag atgacatggt caatgaattg tttgacagcc tgtttccagt catctatacc    540
cagctaatga acccaggcct gcctgattca gccttggaca tcaatgagtg cctccgagga    600
gcaagacgtg acctgaaagt atttgggaat tcccccaagc ttattatgac ccaggttttcc    660 aagtcactgc aagtcactag gatcttcctt caggctctga tcttggaat tgaagtgatc    720 aacacaactg atcacctgaa gttcagtaag gactgtggcc gaatgctcac cagaatgtgg    780
tactgctctt actgccaggg actgatgatg gttaaaccct gtggcggtta ctgcaatgtg    840
gtcatgcaag gctgtatggc aggtgtggtg gagattgaca gtactggag agaatacatt    900 ctgtcccttg aagaacttgt gaatggcatg tacagaatct atgacatgga gaacgtactg    960
cttggtctct tttcaacaat ccatgattct atccagtatg tccagaagaa tgcaggaaag   1020
ctgaccacca ctattggcaa gttatgtgcc cattctcaac aacgccaata tagatctgct   1080
tattatcctg aagatctctt tattgacaag aaagtattaa agttgctca tgtagaacat   1140 gaagaaacct tatccagccg aagaagggaa ctaattcaga gttgaagtc tttcatcagc   1200 ttctatagtg ctttgcctgg ctacatctgc agccatagcc ctgtggcgga aaacgacacc   1260
ctttgctgga tggacaagaa actcgtggag agatacagcc aaaaggcagc aaggaatgga   1320
atgaaaaacc agttcaatct ccatgagctg aaaatgaagg gccctgagcc agtggtcagt   1380
caaattattg acaaactgaa gcacattaac cagctcctga gaaccatgtc tatgcccaaa   1440
ggtagagttc tggataaaaa cctggatgag gaagggtttg aaagtggaga ctgcggtgat   1500
gatgaagatg agtgcattgg aggctctggt gatggaatga taaaagtgaa gaatcagctc   1560
```

```
cgcttccttg cagaactggc ctatgatctg gatgtggatg atgcgcctgg aaacagtcag      1620
caggcaactc cgaaggacaa cgagataagc acctttcaca acctcgggaa cgttcattcc      1680
ccgctgaagc ttctcaccag catggccatc tcggtggtgt gcttcttctt cctggtgcac      1740
tga                                                                   1743
```

```
<210> SEQ ID NO 20
<211> LENGTH: 580
<212> TYPE: PRT
<213> ORGANISM: Homo sapiens

<400> SEQUENCE: 20

Met Ala Gly Thr Val Arg Thr Ala Cys Leu Val Ala Met Leu Leu
1               5                   10                  15

Ser Leu Asp Phe Pro Gly Gln Ala Gln Pro Pro Pro Pro Pro Asp
            20                  25                  30

Ala Thr Cys His Gln Val Arg Ser Phe Phe Gln Arg Leu Gln Pro Gly
                35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335
```

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Glu Thr Leu
            370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
            405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
            435                 440                 445

Glu Leu Lys Met Lys Gly Pro Glu Pro Val Val Ser Gln Ile Ile Asp
            450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
            485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
            515                 520                 525

Asp Leu Asp Val Asp Asp Ala Pro Gly Asn Ser Gln Gln Ala Thr Pro
530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
            565                 570                 575

Phe Leu Val His
            580

<210> SEQ ID NO 21
<211> LENGTH: 115
<212> TYPE: PRT
<213> ORGANISM: Artificial Sequence
<220> FEATURE:
<223> OTHER INFORMATION: Humanized antibody H-chain variable region

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Trp Gly Gln Gly Thr Leu Val Thr
            100                 105                 110

```
Val Ser Ser
        115

<210> SEQ ID NO 22
<211> LENGTH: 112
<212> TYPE: PRT
<213> ORGANISM: Artificial Sequence
<220> FEATURE:
<223> OTHER INFORMATION: Humanized antibody L-chain variable region

<400> SEQUENCE: 22

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 23
<211> LENGTH: 5
<212> TYPE: PRT
<213> ORGANISM: Mus musculus

<400> SEQUENCE: 23

Asp Tyr Glu Met His
1               5

<210> SEQ ID NO 24
<211> LENGTH: 17
<212> TYPE: PRT
<213> ORGANISM: Mus musculus

<400> SEQUENCE: 24

Ala Leu Asp Pro Lys Thr Gly Asp Thr Ala Tyr Ser Gln Lys Phe Lys
1               5                   10                  15

Gly

<210> SEQ ID NO 25
<211> LENGTH: 6
<212> TYPE: PRT
<213> ORGANISM: Mus musculus

<400> SEQUENCE: 25

Phe Tyr Ser Tyr Thr Tyr
1               5

<210> SEQ ID NO 26
<211> LENGTH: 16
<212> TYPE: PRT
<213> ORGANISM: Mus musculus

<400> SEQUENCE: 26

Arg Ser Ser Gln Ser Leu Val His Ser Asn Gly Asn Thr Tyr Leu His
1               5                   10                  15
```

<210> SEQ ID NO 27
<211> LENGTH: 7
<212> TYPE: PRT
<213> ORGANISM: Mus musculus

<400> SEQUENCE: 27

Lys Val Ser Asn Arg Phe Ser
1               5

<210> SEQ ID NO 28
<211> LENGTH: 9
<212> TYPE: PRT
<213> ORGANISM: Mus musculus

<400> SEQUENCE: 28

Ser Gln Asn Thr His Val Pro Pro Thr
1               5

<210> SEQ ID NO 29
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu 245                 250                 255
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 30
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly

```
                165                 170                 175
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Leu Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 31
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
```

```
                        85                  90                  95
Thr Arg Phe Tyr Ser Tyr Thr Tyr Trp Gly Gln Gly Thr Leu Val Thr
                       100                 105                 110

Val Ser Ser Ala Ser Thr Lys Gly Pro Ser Val Phe Pro Leu Ala Pro
                       115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ala Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 32
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 32

Gln Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Thr Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
        435                 440                 445

<210> SEQ ID NO 33
<211> LENGTH: 445
<212> TYPE: PRT
<213> ORGANISM: Artificial Sequence
<220> FEATURE:
<223> OTHER INFORMATION: Humanized antibody H-chain

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ala Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Glu Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

```
Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
        435                 440                 445

<210> SEQ ID NO 34
<211> LENGTH: 217
<212> TYPE: PRT
<213> ORGANISM: Homo sapiens

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Glu Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 35
<211> LENGTH: 217
<212> TYPE: PRT
<213> ORGANISM: Homo sapiens

<400> SEQUENCE: 35

Ala Pro Glu Leu Leu Gly Gly Pro Asp Val Phe Leu Phe Pro Pro Lys
1               5                   10                  15
```

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Leu Pro Glu Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 36
<211> LENGTH: 217
<212> TYPE: PRT
<213> ORGANISM: Homo sapiens

<400> SEQUENCE: 36

Ala Pro Glu Leu Leu Gly Gly Pro Asp Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ala Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Glu Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu

```
                    165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 37
<211> LENGTH: 217
<212> TYPE: PRT
<213> ORGANISM: Homo sapiens

<400> SEQUENCE: 37

Ala Pro Glu Leu Leu Gly Gly Pro Asp Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Thr
                85                  90                  95

Ala Leu Pro Ala Pro Glu Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 38
<211> LENGTH: 217
<212> TYPE: PRT
<213> ORGANISM: Homo sapiens

<400> SEQUENCE: 38

Ala Pro Glu Leu Leu Gly Gly Pro Asp Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
```

```
                  50                  55                  60
Gln Tyr Asn Ala Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Glu
                 85                  90                  95

Ala Leu Pro Ala Pro Glu Lys Thr Ile Ser Lys Ala Lys Gly Gln
                100                 105                 110

Pro Arg Glu Pro Gln Val Tyr Thr Leu Pro Pro Ser Arg Asp Glu Leu
                115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```